US007498427B2

(12) United States Patent
Booth et al.

(10) Patent No.: US 7,498,427 B2
(45) Date of Patent: Mar. 3, 2009

(54) NUCLEOTIDE SEQUENCES OF A NEW CLASS OF DIVERGED DELTA-9 STEAROYL-ACP DESATURASE GENES

(75) Inventors: John R. Booth, Boothywn, PA (US); Rebecca E. Cahoon, Webster Groves, MO (US); William D. Hitz, Wilmington, DE (US); Anthony J. Kinney, Wilmington, DE (US); Narendra S. Yadav, Chadds Ford, PA (US)

(73) Assignee: E. I. Du Pont DeNemours & Company, Wilmington, DE (US)

( * ) Notice: Subject to any disclaimer, the term of this patent is extended or adjusted under 35 U.S.C. 154(b) by 453 days.

(21) Appl. No.: 10/981,293

(22) Filed: Nov. 4, 2004

(65) Prior Publication Data
US 2005/0066390 A1    Mar. 24, 2005

Related U.S. Application Data

(63) Continuation of application No. 09/934,900, filed on Aug. 22, 2001, now abandoned.

(60) Provisional application No. 60/226,996, filed on Aug. 22, 2000.

(51) Int. Cl.
C07H 21/04    (2006.01)
C12N 15/82   (2006.01)
(52) U.S. Cl. ............... 536/23.2; 435/419; 435/252.3
(58) Field of Classification Search ............... None
See application file for complete search history.

(56) References Cited

U.S. PATENT DOCUMENTS

| 4,683,195 A | 7/1987 | Mullis et al. |
| 4,800,159 A | 1/1989 | Mullis et al. |
| 4,945,050 A | 7/1990 | Sanford et al. |
| 5,107,065 A | 4/1992 | Shewmaker et al. |
| 5,190,931 A | 3/1993 | Inouye |
| 5,231,020 A | 7/1993 | Jorgensen et al. |
| 5,283,323 A | 2/1994 | Berzofsky et al. |
| 5,443,974 A | 8/1995 | Hitz et al. |
| 5,723,595 A | 3/1998 | Thompson et al. |
| 5,760,206 A | 6/1998 | Hitz et al. |
| 5,952,544 A | 9/1999 | Browse et al. |

FOREIGN PATENT DOCUMENTS

| EP | 0242236 B2 | 10/1987 |
| EP | 0301749 A2 | 2/1989 |
| WO | 91/13972 A1 | 9/1991 |
| WO | 91/18985 A1 | 12/1991 |
| WO | 93/11245 A1 | 6/1993 |
| WO | 94/11516 A1 | 5/1994 |

OTHER PUBLICATIONS

Bork et al, TIG 12(10): 425-427, Oct. 1996.*
Brenner, S., TIG 15(4): Apr. 1999.*
Smith et al, Nature Biotechnology 15: 1222-1223, Nov. 1997.*
Doerks et al, TIG 14(6): Jun. 1998.*
Broun et al, Science 282: 1315-1317, Nov. 13, 1998.*
Van de Loo et al, PNAS, USA 92:6743-6747, Jul. 1995.*
De Luca, V. AgBiotech News and Information 5(6): 225N-229N, 1993.*
GenEMBL Accession AF139377, Mar. 17, 2000.*
Fred H. Mattson et al., J. Lipid Res., vol. 26;194-202, 1985, Comparison of Effects of Dietary Saturated, Monounsaturated, and Polyunsaturated Fatty Acids on Plasma Lipids and Lipoproteins in Man.
Scott M. Grundy et al., New England J. of Med., vol. 314:745-748, 1986, Comparison of Monounsaturated Fatty Acids and Carbohydrates for Lowering Plasma Cholesterol.
Ronald P. Mensink et al., The Lancet, vol. 1:122-125, 1987, Effect of Monounsaturated Fatty Acids Versus Complex Carbohydrates on High-Density Lipoproteins in Healthy Men and Women.
Robert S. Goldberg et al., Cell, vol. 56:149-160, 1989, Regulation of Gene Expression During Plant Embryogenesis.
Alexander R. Van Der Krol et al., Gene, vol. 72:45-50, 1988, Antisense Genes in Plants: An Overview.
Paula P. Chee et al., Plant Phys., vol. 91:1212-1218, 1989, Transformation of Soybean (Glycine Max) by Infecting Germinating Seeds With Agrobacterium Tumefaciens.
Paul Christou et al., PNAS, vol. 86:7500-7504, 1989, Inheritance and Expression of Foreign Genes in Transgenic Soybean Plants.
Maud A. W. Hinchee et al., Bio/Technology, vol. 6:915-922, 1988, Production of Transgenic Soybean Plants Using Agrobacterium-Mediated DNA Transfer.
Marc De Block et al., Plant Phys., vol. 91:694-701, 1989, Transformation of Brassica Napus and Brassica Oleracea Using Agrobacterium Tumefaciens and the Expression of the Bar and Neo Genes in the Transgenic Plants.
N. P. Everett et al., Bio/Technology, vol. 5:1201-1204, 1987, Genetic Engineering of Sunflower (Helianthus Annuus L.).
S. D. Tanksley et al., Bio/Technology, vol. 7:257-264, 1989, RFLP Mapping in Plant Breeding: New Tools for an Old Science.
John Harwood, Critical Reviews in Plant Sciences, vol. 8(1):1-43, 1989, Lipid Metabolism in Plants.
Thomas A. McKeon et al., J. Biol. Chem., vol. 257:12141-12147, 1982, Purification and Characterization of the Stearoyl-ACYL Carrier Protein Desaturase and the ACYL-ACYL Protein Thioesterase From Maturing Seeds of Safflower.
Maureen Bafor et al., JAOCS, vol. 67:217-225, 1990, Properties of the Glycerol Acylating Enzymes in Microsomal Preparations From the Developing Seeds of Safflower (Carthamus Tinctorius) and Turnip Rape (Brassica Campestris) and Their Ability to Assemble Cocoa-Butter Type Fats.
Mark A. Thiede et al., J. Biol. Chem., vol. 262:13230-13235, 1986, Construction and Sequence of CDNA for Rat Liver Stearyl Coenzyme a Desaturase.

(Continued)

*Primary Examiner*—Elizabeth F McElwain

(57) ABSTRACT

An isolated nucleic acid fragment encoding a diverged delta-9 fatty acid desaturase is disclosed. Also the construction of a chimeric gene encoding all or a portion of the diverged delta-9 fatty acid desaturase is disclosed, in sense or antisense orientation, wherein expression of the chimeric gene results in production of altered levels of the diverged delta-9 fatty acid desaturase in a transformed host cell.

9 Claims, 2 Drawing Sheets

OTHER PUBLICATIONS

James M. Ntambi et al., J. Biol. Chem., vol. 263:17291-17300, 1988, Differentiation-Induced Gene Expression in 3T3-L1 Preadipocytes.

Klaus H. Kaestner et al., J. Biol. Chem., vol. 264:14755-17461, 1989, Differentiation-Induced Gene Expression in 3T3-L1 Preadipocytes.

Philipp Strittmatter et al., J. Biol. Chem., vol. 263:2532-2535, 1988, Bacterial Synthesis of Active Rate Stearyl-COA Desaturase Lacking the 26-Residue Amino-Terminal Amino Acid Sequence.

Gregory A. Thompson et al., PNAS, vol. 88:2578-2582, 1991, Primary Structures of the Precursor and Mature Forms of Stearoyl-ACYL Carrier Protein Desaturase From Safflower Embryos and Requirement of Ferredoxin for Enzyme Activity.

John Shanklin et al., PNAS, vol. 88:2510-2514, 1991, Stearoyl-ACYL-Carrier-Protein Desaturase From Higher Plants is Structurally Unrelated to the Animal and Fungal Homologs.

John Shanklin et al., Plant Phys., vol. 97:467-468, 1991, Sequence of a Complementary DNA From Cucumis Sativus L. Encoding the Stearoyl-ACYL Carrier Protein Desaturase.

National Center for Biotechnology Information General Identifier No. 4704824, Mar. 17, 2000, M. R. Swiderski et al., Identification of New Nodulin CDNAS From Yellow Lupine by Differential Display.

Michael R. Swiderski et al., Plant Science, vol. 151:75-83, 2000, Identification of New Nodulin CDNAS From Yellow Lupine by Differential Display.

National Center for Biotechnology Information General Identifier No. 267036, Mar. 1, 2002, A. Sato et al., Nucleotide Sequence of a Complementary DNA Clone Encoding Stearoyl-ACYL Carrier Protein Desaturase From Simmondsia Chinensis.

A. Sato et al., Plant Phys., vol. 99:362-363, 1992, Nucleotide Sequence of a Complementary DNA Clone Encoding Stearoyl-ACYL Carrier Protein Desaturase From Simmondsia Chinensis.

National Center for Biotechnology Information General Identifier No. 6957724, Jan. 24, 2001, X. Lin et al., Arabidopsis Thaliana Chromosome II BAC F16B3 Genomic Sequence.

National Center for Biotechnology Information General Identifier No. 3355632, Jul. 24, 1998, R. K. Jain et al., Isolation of the Two Flax Stearoyl-ACYL Carrier Protein Desaturase Gene Promoters by the Inverse Polymerase Chain Reaction and Their Differential Regulation in Transgenic Flax, Tobacco, and Canola.

Athel Cornish-Bowden, Nucl. Acids Res., vol. 13:3021-3030, 1985, Nomenclature for Incompletely Specified Bases in Nucleid Acid Sequences: Recommendations.

H.B.F. Dixon et al., Biochem. J., vol. 219(2):345-373, 1984, Nomenclature and Symbolism for Amino Acids and Peptides.

Desmond G. Higgins et al., Cabios., vol. 5:151-153, 1989, Fast and Sensitive Multiple Sequence Alignments on a Microcomputer.

Stephen F. Altschul et al., J. Mol. Biol., vol. 215:403-410, 1993, Basic Local Alignment Search Tool.

Jack K. Okamuro et al., Biochemistry of Plants, vol. 15:1-82, 1989, Regulation of Plant Gene Expression: General Principles.

Roisin Turner et al., Mol. Biotech., vol. 3:225-236, 1995, The Potential Exploitation of Plant Viral Translational Enhancers in Biotechnology for Increased Gene Expression.

Ivan L. W. Ingelbrecht et al., Plant Cell, vol. 1:671-680, 1989, Different 3' End Regions Strongly Influence the Level of Gene Expression in Plant Cells.

Maarten J. Chrispeels, Ann. Rev. Plant Phys., Plant Mol. Biol., vol. 42:21-53, 1991, Sorting of Proteins in the Secretory System.

Natasha Raikhel, Plant Phys., vol. 100:1627-1632, 1992, Nuclear Targeting in Plants.

R. Deblaere et al., Meth. Enzymol., vol. 143:277, 1987, Vectors for Cloning in Plant Cells.

T. M. Klein et al., Nature (London), vol. 327:70-73, 1987, High-Velocity Microprojectiles for Delivering Nucleic Acids Into Living Cells.

Michael A. Frohman et al., PNAS, vol. 85:8998-9002, 1988, Rapid Production of Full-Length Rare Transcripts: Amplification Using a Single Oligonucleotide Primer.

Osamu Ohara et al., PNAS, vol. 86:5873-5677, 1989, One-Sided Polymerase Chain Reaction: the Amplification of CDNA.

Elwyn Y. Loh et al., Science, vol. 243:217-220, 1989 Polymerase Chain Reaction With Single-Sided Specificity: Analysis of T Cell Receptor & Chain.

Michael A. Frohman et al., Techniques, vol. 1:165, 1989, Amplification of 3' End CDNAS.

Richard Alan Lerner, Adv. Immunol., vol. 36:1-34, Maniatis, 1984, Antibodies of Predetermined Specificity in Biology and Medicine.

Jonathan D. G. Jones et al., EMBO J., vol. 4:2411-2418, 1985, High Level Expression of Introduced Chimaeric Genes in Regenerated Transformed Plants.

Elionor R. P. De Almeida et al., Mol. Gen. Genetics, vol. 218;78-86, 1989, Transgenic Expression of Two Marker Genes Under the Control of an Arabidopsis RBC2 Promoter: Sequences Encoding the Rubisco Transit Peptide Increase Expression Levels.

Kenneth Keegstra, Cell, vol. 56:247-253, 1989, Transport and Routing of Proteins Into Chloroplasts.

Eric S. Lander et al., Genomics, vol. 1:174-181, 1987, Mapmaker: An Interactive Computer Package for Constructing Primary Genetic Linkage Maps of Experimental and Natural Populations.

David Botstein et al., Am. J. Hum. Genet., vol. 32:314-331, 1980, Construction of a Genetic Linkage Map in Man Using Restriction Fragment Length Polymorphisms.

R. Bernatzsky et al., Plant Mol. Biol. Reporter, vol. 4:37-41, 1986, Methods for Detection of Single or Low Copy Sequences in Tomato on Southern Blots.

Jorg D. Hoheisel et al., Nonmammalian Genomic Analysis: A Practical Guide, Academic Press, 1996, pp. 319-346, Integrated Genome Mapping by Hybridization Techniques.

Barbara J. Trask, Trends Genet., vol. 7:149-154, 1991, Fluorescent in Situ Hybridization: Applications in Cytogenetics and Gene Mapping.

Maris Laan et al., Genome Res., vol. 5:13-20, 1995, Mechanically Stretched Chromosomes as Targets for High-Resolution Fish Mapping.

Haig H. Kazazain, J. Lab. Clin. Med., vol. 11:95-96, 1989, Diagnosis by Gene Amplification.

Val C. Sheffield et al., Genomics, vol. 16:325-332, 1993, The Sensitivity of Single-Strand Conformation Polymorphism Analysis for the Detection of Single Base Substitutions.

Ulf Landegren et al., Science, vol. 241:1077-1080, 1988, A Ligase-Mediated Gene Detection Technique.

Boris P. Sokolov, Nucl. Acids Res., vol. 18:3671, 1990, Primer Extension Technique for the Detection of Single Nucleotide in Genomic DNA.

Michael A. Walter et al., Nat. Genet., vol. 7:22-28, 1997, A Method for Constructing Radiation Hybrid Maps of Whole Genomes.

P. H. Dear et al., Nucl. Acid. Res., vol. 17:6795-6807, 1989, Happy Mapping: A Proposal for Linkage Mapping the Human Genome.

Dennis G. Ballinger et al., PNAS, vol. 86:9402-9406, 1989, Targeted Gene Mutations in Drosophila.

Ronald Koes et al., PNAS, vol. 92:8149-8153, 1995, Targeted Gene Inactivation in Petunia by PCR-Based Selection of Transposon Insertion Mutants.

Robert J. Bensen et al., Plant Cell, vol. 7:75-84, 1995, Cloning and Characterization of the Maize AN1 Gene.

Mark D. Adams et al., Science, vol. 252:1651-1656, 1991, Complementary DNA Sequencing: Expressed Sequence Tags and Human Genome Project.

Scott E. Devine et al., Nucl. Acid. Res., vol. 22:3765-2772, 1994, Efficient Integration of Artificial Transposons Into Plasmid Targets in Vitro: a Useful Tool for DNA Mapping, Sequencing and Genetic Analysis.

Mary E. Fling et al., Nucl. Acid Res., vol. 11:5147-5158, 1983, The Nucleotide Sequence of the Trimethoprim-Resistant Dihydrofolate Reductase Gene Harbored by TN7.

Warren Gish et al., Nat. Genet., vol. 3:266-272, 1993, Identification of Protein Coding Regions by Database Similarity Search.

Stephen F. Altschul et al., Nucl. Acid Res., vol. 25:3389-3402, Gapped Blast and PSI-Blast: A New Generation of Protein Database Search Programs.

National Center for Biotechnology Information General Identifier No. 417820, Mar. 1, 2002, J. Shanklin et al., Sequence of a Complementary DNA From Cucumis Sativus'L. Encoding the Stearoyl-ACYL-Carrier Protein Desaturase.

National Center for Biotechnology Information General Identifier No. 7523660, Apr. 7, 2000, N. A. Federspeil et al.

Chen Jia-Qi et al., Sci. Sin Peking, vol. 18:659-668, 1975, The Important Role of Historical Flood Data in the Estimation of Spillway Design Floods.

Joan T. Odell et al., Nature, vol. 313:810-812, 1985, Identification of DNA Sequences Required for Activity of the Cauliflower Mosaic Virus 35S Promoter.

Michael E. Fromm et al., Bio/Technology, vol. 8:833-839, 1990, Inheritance and Expression of Chimeric Genes in the Progeny of Transgenic Maize Plants.

Jeff J. Doyle et al., J. Biol. Chem., vol. 261:9228-9238, 1986, The Glycosylated Seed Storage Proteins of Glycine Max and Phaseolus Vulgaris.

Linda Gritz et al., Gene, vol. 25:179-188, 1983, Plasmid-Encoded Hygromycin B Resistance: The Sequence of Hygromycin B Phosphototransferase Gene and Its Expression in *Escherichia coli* and *Saccharomyces cerevisiae*.

Alan H. Rosenberg et al., Gene, vol. 56:125-135, 1987, Vectors for Selective Expression of Cloned DNAS by T7 RNA Polymerase.

F. William Studier et al., J. Mol. Biol., vol. 189:113-130, 1986, Use of Bacteriophage T7 RNA Polymerase to Direct Selective High-Level Expression of Cloned Genes.

\* cited by examiner

```
                                                                                                                77
SID2  (soy)   M--LSIIFKEFVKYNRHVIKTMQIRTCHSITTQTLPQ--LPCSSRKAHHRHLLPPLNAAVSAAP-FKARKAHS------MPPEKKEIF
SID10 (corn)  MAATTPLLAVAGHGVSYKPANAKDSYYCFKFASSARTRVTLPQIIHWRCRSSHSSTGTTMAVPVLKRREKQDEEQEWMGYLAPEKLEVL
SID12 (corn)  M--QAHGI-------AIRARGPVAATQAPARR--RQC-------RVSAAAVGAP----AARARVTHS-------MPPEKAEVF
SID14 (rice)  ----------------------------------------------------------------------------------
SID16 (rice)  M--QVVG--------------TVRVSGGCGAVVAPS--R--RQC-------RVSAAVLTAAETATATRRRVTHS------MPPEKAEVF
gi4704824     M-----------------QIQTCYSIRIQILP---LP-WARRTGRHKMLPPIAAISATPPSLKSPKTHS-------MPPEKIEIF
gi267036      MALKLHTAFNPSM--AVTSSGLPRSYHL----RSHRVFMASSTIGITS-KEIPNAKKPHMPPREAHVQKTHS-------MPPQKIEIF
gi6957724     MALLLNSTITVAMKQNPLVAVSFPRTTCLGSSFSPPRLLRVSCVATNPSKTSEETDKKKFRPIKEVPNQVTHT------ITQEKLEIF
gi3355632     MALKLNPVTTFPS-------TRSLNNFSSR----SPRTFLMAASTFNSTSTKEAEKLKKSHGPPKEVHMQVTHS-------MPPQKLEIF
SID23 (soy)   MALRLNPIPT--Q------TFSLPQMPSL-----RSPRFRMASTL--RSGSKEVENIKKPFTPPREVHVQVTHS-------MPPQKIEIF 166
SID2  (soy)   KSLEGWASEWVLPLLKPVEQCWQPQNFLPDPS-LPHEEFSHQVKELRERTKELPDEYFVVLGDMVTEDALPTYQTMINNLDGVKDDSGT
SID10 (corn)  AHLEPWAEAHVLPLLKPAEEAWQPSDMLPDPAALGDEGFHDACRELRARAASVPDAHLVCLVGNMITEEALPTYQSVPNRFEAVRDLTGA
SID12 (corn)  RSLEGWAARSLLPLLKPVEECWQPADFLPDSS---SEMFGHEVRELRARAAGLPDEYFVVLVGDMVTEEALPTYQTMINTLDGVRDETGA
SID14 (rice)  ----------------------------------------------------------------------------------
SID16 (rice)  RSLEGWARSSLLPLLKPVEECWQPTDFLPDSS----SEMFEHQVHELRARAAGLPDEYFVVLVGDMITEEALPTYQTMINTLDGVRDETGA
gi4704824     KSLESWASQSVLPLLKPVEQCWQPQEFVPDSS-LPFGDFTDQVKALRDRTAELPEEYFVVLVGDMITEDALPTYQSMINNLDGVRDETGS
gi267036      KSLEGWAEENVLVHLKPVEKCWQPQDFLPDPA--SEG-FMDQVKELRERTKEIPDEYLVVLVGDMITEEALPTYQTMLNTLDGVRDETGA
gi6957724     KSMENWAQENLLSYLKPVEASWQPQDFLPETN--DEDRFYEQVKELRDRTKEIPDDYFVVLVGDMITEEALPTYQTLNTLDGVKDETGG
gi3355632     KSLEGWAEDVLLPHLKPVEKCWQPQDFLPEPE--SDG-FEEQVKELRARAKELPDDYFVVLVGDMITEEALPTYQTMLNTLDGVRDETGA
SID23 (soy)   KSLEDWADQNILTHLKPVEKCWQPQDFLPDPS--SDG-FEEQVKELRERAKEIPDDYFVVLVGDMITEEALPTYQTMLNTLDGVRDETGA 254
SID2  (soy)   SPSPWAVMTRAWTAEENRHGDLLRTYLYLSGRVDMAKVEKTVHYLISAGMDPGTDNNPYLGFVYTSFQERATFVAHGNTARL--AKEGGD
SID10 (corn)  DSTAWARMIRGWSAEENRHGDALSHYMYLSGRVDMRQVDRTVHRLIASGMAMNAARSPYHGFIYVAFQERATAISHGNMARHVGA--HGD
SID12 (corn)  SNCPWAVWTRAWTAEENRHGDILGKYMYLSGRVDMRMVEKTVQYLIGSGMDPGTENNPYLGFVYTSFQERATAVSHGNTARL--ARAHGD
SID14 (rice)  -------------------YLSGRFDMAEVERAVHRLIRSGMAVDPPCSPYHAFVYTAFQERATAVAHGNTARLVGARGHGD
SID16 (rice)  SACPWAVWTRTWTAEENRHGDILGKYMYLSGRVDMRMVEKTVQYLIGSGMDPGTENNPYLGFVYTSFQERATAVSHGNTARL--ARAHGD
gi4704824     SPSPWALWTRAWTAEEKRHGDLLRTYLYLSGRVDMKKIEKTVQYLIGSGMDPGTENNPYLGFVYTSFQERATFVSHGNTARL--AKEGGD
gi267036      SLTSWAIWTRAWTAEENRHGDLLNKYLYLTGRVDMKQIEKTIQYLIGSGMDPRSENNPYLGFIYTSFQERATFISHGNTARL--AKDHGD
gi6957724     SLTPWAVWVRAWTAEENRHGDLLNKYLYLSGRVDMRHVEKTIQYLIGSGMDSKFENNPYNGFIYTSFQERATFISHGNTAKL--ATTYGD
gi3355632     SLTPWAINTRAWTAEENRHGDLLNKYLYLSGRVDMRQIEKTIQYLIGSGMDPKTENNPYLGFIYTSFQERATFISHGNTARL--AKDHGD
SID23 (soy)   SLTSWAIWTRAWTAEENRHGDLLNKYLYLSGRVDMKQIEKTIQYLIGSGMDPRTENSPYLGFIYTSFQERATFISHGNTARL--AKEHGD
```

FIG. 1-1

```
              255                                                                                                   344
SID2  (soy)   PVLARLCGTIAADEKRHENAYSRIVEKLLEVDPTGAMVAIGNMMEKKITMPAHLMYDGDDPRLFEHYSAVAQRIGVYTANDYADILEFLV
SID10 (corn)  HVLARVCGAIMADEKRHETAYTRIVAKLFEVDPDAAVRALGYMMRHRITMPAALMTDGRDAHLYAHYAAAAQTGVYTASDYRSILEHLI
SID12 (corn)  DVLARACGTIAADEKRHETAYGRIVEQLLQLDPEGAVLAVADMRKRITMPAHLMHDGRDMDLFEHFAAVAQRLGVYTARDYADIVEFLV
SID14 (rice)  AALARVCGTVAADEKRHEAAYTRIVSRLLEADPDAGVRAVARMLRRGVAMPTSPISDGRRDDLYACVVSLAEQAGTYTVSDYCSIVEHLV
SID16 (rice)  DVLARTCGTIAADEKRHETAYGRIVEQLLRLDPDGAMLAIADMMHKRITMPAHLMHDGRDMNLFDHFAAVAQRLNVYTARDYADIVEFLV
gi4704824     PVLARICGTIAADEKRHENAYSRIVEKLLELDPTGAMVAIGDMMQKKITMPAHLMYDGEDPKLFDHFSAVAQRMGVYTANDYADILEFLI
gi267036      FQLAQVCGIIAADEKRHETAYTKIVEKLFEIDPDGAVLALADMRKKVSMPAHLMYDGKDDNLFENYSAVAQQIGVYTAKDYADILEHLV
gi6957724     TTLAKICGTIAADEKRHETAYTRIVEKLFEIDPDGTVQALASMRKRITMPAHLMHDGRDDDLFDHYAAVAQRIGVYTATDYAGILEFLL
gi3355632     MKLAQICGIIAADEKRHETAYTKIVEKLFEIDPDGTVLALADMRKKISMPAHLMYDGEDDNLFDNYSSVAQRIGVYTAKDYADILEFLV
SID23 (soy)   IKLAQICGMIASDEKRHETAYTKIVEKLFEVDPDGTVMAFADMRKKIAMPAHLMYDGRDDNLFDNYSAVAQRIGVYTAKDYADILEFLV 345                                                         405
SID2  (soy)   ERWRLEKLE-GLMAEGKRAQDFVCGLAPRIRRLQERADERARKMKKHHG-VKFSWIFNKE---LLL  (405 aa)
SID10 (corn)  RQWRVEELAAGLSGEGRRARDYVCGLPHKIRRMEEKAHDRAAQTQKKPTSVPFSWIFDRSVNVVIP   (424 aa)
SID12 (corn)  KRWKLETLESGLSGEGRRARDFVCGLAPRMRRAAERAEDRAKK-DEPRM-VKFSWIFDRE---AVV   (380 aa)
SID14 (rice)  REWRVEELAAGLSGEGRRARDYVCELPQKIRRMKEKAHERAVKAQKKPISIPINWIFDRHVSVMLP  (219 aa)
SID16 (rice)  KRWKLETLETGLSGEGRRARDFVCGLAKRMRRAAERAEDRAKK-DEQRK-VKFSWIYDRE---IIL   (381 aa)
gi4704824     GRWRLEKVQ-DLKDEGKKAQDFVCGLAPRIRRLQERADERARKMK-PHA-VKFSWIFNKE---LKV   (384 aa)
gi267036      NRWKVENL-MGLSGEGHKAQDFVCGLAPRIRKLGERAQSLSKPVS-L---VPFSWIFNKE---VEL   (398 aa)
gi6957724     RRWEVEKLGMGLSGEGRRAQDYLCTLPQRIRRLEERANDRVKLASKSKPSVSFSWIYGRE---VEL   (411 aa)
gi3355632     GRWKVDAF-TGLSGEGNKAQDFVCGLPARIRKLEERAAGRAKQTSKS---VPFSWIFSRE---LVL   (396 aa)
SID23 (soy)   GRWKVEQL-TGLSGEGRKAQEYVCGLPPRIRRLEERAQARGKESS-T---LKFSWIHDRE---VLL   (391 aa)
```

FIG. 1-2

NUCLEOTIDE SEQUENCES OF A NEW CLASS OF DIVERGED DELTA-9 STEAROYL-ACP DESATURASE GENES

This application claims the benefit of U.S. Provisional Application No. 60/226,996, filed Aug. 22, 2000, the entire contents of which are herein incorporated by reference.

FIELD OF THE INVENTION

This invention is relates to the field of plant molecular biology and, in particular, to nucleic acid fragments encoding a diverged delta-9 fatty acid desaturase in plants and seeds.

BACKGROUND OF THE INVENTION

Soybean oil accounts for about 70% of the 14 billion pounds of edible oil consumed in the United States and is a major edible oil worldwide. It is used in baking, frying, salad dressing, margarine, and a multitude of processed foods. In 1987/88 60 million acres of soybean were planted in the U.S. Soybean is the lowest-cost producer of vegetable oil, which is a by-product of soybean meal. Soybean is agronomically well-adapted to many parts of the U.S. Machinery and facilities for harvesting, storing, and crushing are widely available across the U.S. Soybean products are also a major element of foreign trade since 30 million metric tons of soybeans, 25 million metric tons of soybean meal, and 1 billion pounds of soybean oil were exported in 1987/88. Nevertheless, increased foreign competition has lead to recent declines in soybean acreage and production. The low cost and ready availability of soybean oil provides an excellent opportunity to upgrade this commodity oil into higher value speciality oils to both add value to soybean crop for the U.S. farmer and enhance U.S. trade.

Soybean oil derived from commercial varieties is composed primarily of 11% palmitic (16:0), 4% stearic (18:0), 24% oleic (18:1), 54% linoleic (18:2) and 7% linolenic (18:3) acids. Palmitic and stearic acids are, respectively, 16- and 18-carbon-long saturated fatty acids. Oleic, linoleic and linolenic are 18-carbon-long unsaturated fatty acids containing one, two and three double bonds, respectively. Oleic acid is also referred to as a monounsaturated fatty acid, while linoleic and linolenic acids are also referred to as polyunsaturated fatty acids. The specific performance and health attributes of edible oils is determined largely by their fatty acid composition.

Soybean oil is high in saturated fatty acids when compared to other sources of vegetable oil and contains a low proportion of oleic acid, relative to the total fatty acid content of the soybean seed. These characteristics do not meet important health needs as defined by the American Heart Association.

More recent research efforts have examined the role that monounsaturated fatty acid plays in reducing the risk of coronary heart disease. In the past, it was believed that monounsaturates, in contrast to saturates and polyunsaturates, had no effect on serum cholesterol and coronary heart disease risk. Several recent human clinical studies suggest that diets high in monounsaturated fat may reduce the "bad" (low-density lipoprotein) cholesterol while maintaining the "good" (high-density lipoprotein) cholesterol. [See Mattson et al. (1985) *Journal of Lipid Research* 26:194-202, Grundy (1986) *New England Journal of Medicine* 314:745-748, and Mensink et al. (1987) *The Lancet* 1:122-125, all collectively herein incorporated by reference.] These results corroborate previous epidemiological studies of people living in Mediterranean countries where a relatively high intake of monounsaturated fat and low consumption of saturated fat correspond with low coronary heart disease mortality. [Keys, A., Seven Countries: A Multivariate Analysis of Death and Coronary Heart Disease, Cambridge: Harvard University Press, 1980, herein incorporated by reference.] The significance of monounsaturated fat in the diet was further confirmed by international researchers from seven countries at the Second Colloquim on Monounsaturated Fats held Feb. 26, 1987, in Bethesda, Md., and sponsored by the National Heart, Lung and Blood Institutes [Report, Monounsaturates Use Said to Lower Several Major Risk Factors, Food Chemical News, Mar. 2, 1987, p. 44, herein incorporated by reference].

Soybean oil is also relatively high in polyunsaturated fatty acids—at levels in far excess of our essential dietary requirement. These fatty acids oxidize readily to give off-flavors and result in reduced performance associated with unprocessed soybean oil. The stability and flavor of soybean oil is improved by hydrogenation, which chemically reduces the double bonds. However, the need for this processing reduces the economic attractiveness of soybean oil.

A soybean oil low in total saturates and polyunsaturates and high in monounsaturate would provide significant health benefits to the United States population, as well as, economic benefit to oil processors. Soybean varieties which produce seeds containing the improved oil will also produce valuable meal as animal feed.

Another type of differentiated soybean oil is an edible fat for confectionary uses. More than 2 billion pounds of cocoa butter, the most expensive edible oil, are produced worldwide. The U.S. imports several hundred million dollars worth of cocoa butter annually. The high and volatile prices and uncertain supply of cocoa butter have encouraged the development of cocoa butter substitutes. The fatty acid composition of cocoa butter is 26% palmitic, 34% stearic, 35% oleic and 3% linoleic acids. About 72% of cocoa butter's triglycerides have the structure in which saturated fatty acids occupy positions 1 and 3 and oleic acid occupies position 2. Cocoa butter's unique fatty acid composition and distribution on the triglyceride molecule confer on it properties eminently suitable for confectionary end-uses: it is brittle below 27° C. and depending on its crystalline state, melts sharply at 25-30° C. or 35-36° C. Consequently, it is hard and non-greasy at ordinary temperatures and melts very sharply in the mouth. It is also extremely resistant to rancidity. For these reasons, producing soybean oil with increased levels of stearic acid, especially in soybean lines containing higher-than-normal levels of palmitic acid, and reduced levels of unsaturated fatty acids is expected to produce a cocoa butter substitute in soybean. This will add value to oil and food processors as well as reduce the foreign import of certain tropical oils.

Only recently have serious efforts been made to improve the quality of soybean oil through plant breeding, especially mutagenesis, and a wide range of fatty acid composition has been discovered in experimental lines of soybean (Table 1). These findings (as well as those with other oilcrops) suggest that the fatty acid composition of soybean oil can be significantly modified without affecting the agronomic performance of a soybean plant. However, there is no soybean mutant line with levels of saturates less than those present in commercial canola, the major competitor to soybean oil as a "healthy" oil.

TABLE 1

Range of Fatty Acid Percentages
Produced by Soybean Mutants

| Fatty Acids | Range of Percentages |
|---|---|
| Palmitic Acid | 6-28 |
| Stearic Acid | 3-30 |
| Oleic Acid | 17-50 |
| Linoleic Acid | 35-60 |
| Linolenic Acid | 3-12 |

There are serious limitations to using mutagenesis to alter fatty acid composition. It is unlikely to discover mutations a) that result in a dominant ("gain-of-function") phenotype, b) in genes that are essential for plant growth, and c) in an enzyme that is not rate-limiting and that is encoded by more than one gene. Even when some of the desired mutations are available in soybean mutant lines their introgression into elite lines by traditional breeding techniques will be slow and expensive, since the desired oil compositions in soybean are most likely to involve several recessive genes.

Recent molecular and cellular biology techniques offer the potential for overcoming some of the limitations of the mutagenesis approach, including the need for extensive breeding. Particularly useful technologies are: a) seed-specific expression of foreign genes in transgenic plants [see Goldberg et al.(1989) *Cell* 56:149-160], b) use of antisense RNA to inhibit plant target genes in a dominant and tissue-specific manner [see van der Krol et al. (1988) *Gene* 72:45-50], c) transfer of foreign genes into elite commercial varieties of commercial oilcrops, such as soybean [Chee et al. (1989) *Plant Physiol.* 91:1212-1218; Christou et al. (1989) *Proc. Natl. Acad. Sci. U.S.A.* 86:7500-7504; Hinchee et al. (1988) *Bio/Technology* 6:915-922; EPO publication 0 301 749 A2], rapeseed [De Block et al. (1989) *Plant Physiol.* 91:694-701], and sunflower [Everett et al.(1987) *Bio/Technology* 5:1201-1204], and d) use of genes as restriction fragment length polymorphism (RFLP) markers in a breeding program, which makes introgression of recessive traits into elite lines rapid and less expensive [Tanksley et al. (1989) *Bio/Technology* 7:257-264]. However, application of each of these technologies requires identification and isolation of commercially-important genes.

Oil biosynthesis in plants has been fairly well-studied [see Harwood (1989) in *Critical Reviews in Plant Sciences*, Vol. 8(1):1-43]. The biosynthesis of palmitic, stearic and oleic acids occur in the plastids by the interplay of three key enzymes of the "ACP track": palmitoyl-ACP elongase, stearoyl-ACP desaturase and acyl-ACP thioesterase. Stearoyl-ACP desaturase introduces the first double bond on stearoyl-ACP to form oleoyl-ACP. It is pivotal in determining the degree of unsaturation in vegetable oils. Because of its key position in fatty acid biosynthesis it is expected to be an important regulatory step. While the enzyme's natural substrate is stearoyl-ACP, it has been shown that it can, like its counterpart in yeast and mammalian cells, desaturate stearoyl-CoA, albeit poorly [McKeon et al. (1982) *J. Biol. Chem.* 257:12141-12147]. The fatty acids synthesized in the plastid are exported as acyl-CoA to the cytoplasm. At least three different glycerol acylating enzymes (glycerol-3-P acyltransferase, 1-acyl-glycerol-3-P acyltransferase and diacylglycerol acyltransferase) incorporate the acyl moieties from the cytoplasm into triglycerides during oil biosynthesis. These acyltransferases show a strong, but not absolute, preference for incorporating saturated fatty acids at positions 1 and 3 and monounsaturated fatty acid at position 2 of the triglyceride. Thus, altering the fatty acid composition of the acyl pool will drive by mass action a corresponding change in the fatty acid composition of the oil. Furthermore, there is experimental evidence that, because of this specificity, given the correct composition of fatty acids, plants can produce cocoa butter substitutes [Bafor et al. (1990) *JAOCS* 67:217-225].

Based on the above discussion, one approach to altering the levels of stearic and oleic acids in vegetable oils is by altering their levels in the cytoplasmic acyl-CoA pool used for oil biosynthesis. There are two ways of doing this genetically: a) altering the biosynthesis of stearic and oleic acids in the plastid by modulating the levels of stearoyl-ACP desaturase in seeds through either overexpression or antisense inhibition of its gene, and b) converting stearoyl-CoA to oleoyl-CoA in the cytoplasm through the expression of the stearoyl-ACP desaturase in the cytoplasm.

In order to use antisense inhibition of stearoyl-ACP desaturase in the seed, it is essential to isolate the gene(s) or cDNA(s) encoding the target enzyme(s) in the seed, since antisense inhibition requires a high-degree of complementarity between the antisense RNA and the target gene that is expected to be absent in stearoyl-ACP desaturase genes from other species.

The purification and nucleotide sequences of mammalian microsomal stearoyl-CoA desaturases have been published [Thiede et al. (1986) *J. Biol. Chem.* 262:13230-13235; Ntambi et al. (1988) *J. Biol. Chem.* 263:17291-17300; Kaestner et al. (1989) *J. Biol. Chem.* 264:14755-14761]. However, the plant enzyme differs from them in being soluble, in utilizing a different electron donor, and in its substrate-specificities. The purification and the nucleotide sequences for animal enzymes do not teach how to purify the plant enzyme or isolate a plant gene. The purification of stearoyl-ACP desaturase was reported from safflower seeds [McKeon et al. (1982) *J. Biol. Chem.* 257:12141-12147]. However, this purification scheme was not useful for soybean, either because the desaturases are different or because of the presence of other proteins such as the soybean seed storage proteins in seed extracts.

The rat liver stearoyl-CoA desaturase protein has been expressed in *E. coli* [Strittmatter et al. (1988) *J. Biol. Chem.* 263:2532-2535] but, as mentioned above, its substrate specificity and electron donors are quite distinct from that of the plant.

Plant stearoyl-ACP desaturase cDNAs have been cloned from soybean [U.S. Pat. No. 5,760,206, the disclosure of which is hereby incorporated by reference], safflower [Thompson et al. (1991) *Proc. Natl. Acad. Sci.* 88:2578], castor [Shanklin and Somerville (1991) *Proc. Natl. Acad. Sci.* 88:2510-2514], and cucumber [Shanklin et al. (1991) *Plant Physiol.* 97:467-468]. Kutzon et al. [(1992) *Proc. Natl. Acad. Sci.* 89:2624-2648] have reported that rapeseed stearoyl-ACP desaturase when expressed in *Brassica rapa* and *B. napa* in an antisense orientation can result in increase in 18:0 level in transgenic seeds. All of the reported genes have 59-80% identity to each other at the nucleotide and polypeptide level.

U.S. Pat. No. 5,723,595, issued to Thompson et al. on Mar. 3, 1998, describes stearoyl-ACP desaturases from castor and safflower.

U.S. Pat. No. 5,443,974, issued to Hitz et al., on Aug. 22, 1995, describes soybean stearoyl-ACP desaturase.

U.S. Pat. No. 5,760,206, issued to Hitz et al, on Jun. 2, 1998, describes soybean stearoyl-ACP desaturase.

SUMMARY OF THE INVENTION

The present invention concerns an isolated polynucleotide comprising a nucleotide sequence selected from the group consisting of: (a) a nucleotide sequence encoding a polypeptide having delta-9 fatty acid desaturase activity that has at least 80%, 85%, 90%, or 95% identity based on the Clustal method of alignment when compared to a polypeptide selected from the group consisting of SEQ ID NO:2, 4, 6, 8, 10, 12, 14, or 16, or (b) the complement of the nucleotide sequence.

In a second embodiment, it is preferred that the isolated polynucleotide of the claimed invention comprises a nucleotide sequence which comprises a nucleic acid sequence selected from the group consisting of SEQ ID NO:1, 3, 5, 7, 9, 11, 13, or 15 that codes for a polypeptide selected from the group consisting of SEQ ID NO:2, 4, 6, 8, 10, 12, 14, or 16.

In a third embodiment, this invention relates to a chimeric gene comprising an isolated polynucleotide of the present invention operably linked to at least one suitable regulatory sequence.

In a fourth embodiment, the present invention concerns an isolated host cell comprising a chimeric construct of the present invention or an isolated polynucleotide of the present invention. The host cell may be eukaryotic, such as a yeast or a plant cell, or prokaryotic, such as a bacterial cell.

In a fifth embodiment, the invention also relates to a process for producing an isolated host cell comprising a chimeric construct of the present invention or an isolated polynucleotide of the present invention, the process comprising either transforming or transfecting an isolated compatible host cell with a chimeric gene or isolated polynucleotide of the present invention.

In a sixth embodiment, the invention concerns a diverged delta-9 stearoyl desaturase polypeptide of at least 400 amino acids comprising at least 80% identity based on the Clustal method of alignment compared to a polypeptide selected from the group consisting of SEQ ID NO:2, 4, 6, 8, 10, 12, 14, or 16.

In an seventh embodiment, the invention relates to a method of selecting an isolated polynucleotide that affects the level of expression of a diverged delta-9 stearoyl desaturase polypeptide or enzyme activity in a host cell, preferably a plant cell, the method comprising the steps of: (a) constructing an isolated polynucleotide of the present invention or an isolated chimeric construct of the present invention; (b) introducing the isolated polynucleotide or the isolated chimeric cxonstruct into a host cell; (c) measuring the level of the diverged delta-9 stearoyl desaturase polypeptide or enzyme activity in the host cell containing the isolated polynucleotide; and (d) comparing the level of the diverged delta-9 stearoyl desaturase polypeptide or enzyme activity in the host cell containing the isolated polynucleotide with the level of the diverged delta-9 stearoyl desaturase polypeptide or enzyme activity in the host cell that does not contain the isolated polynucleotide.

In an eighth embodiment, the invention concerns a method of obtaining a nucleic acid fragment encoding a substantial portion of a diverged delta-9 stearoyl desaturase polypeptide, preferably a plant diverged delta-9 stearoyl desaturase polypeptide, comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NO:1, 3, 5, 7, 9, 11, 13, or 15, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a diverged delta-9 stearoyl desaturase amino acid sequence.

In a ninth embodiment, this invention relates to a method of obtaining a nucleic acid fragment encoding all or a substantial portion of the amino acid sequence encoding a diverged delta-9 stearoyl desaturase-polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a tenth embodiment, this invention relates to a method of obtaining a nucleic acid fragment encoding all or a substantial portion of the amino acid sequence encoding a diverged delta-9 stearoyl desaturase polypeptide comprising the steps of: probing a cDNA or genomic library with an isolated polynucleotide of the present invention; identifying a DNA clone that hybridizes with an isolated polynucleotide of the present invention; isolating the identified DNA clone; introducing said clone into a construct for expression in a bacteria or yeast; and assaying for delta-9 desaturase activity in the bacteria or yeast.

In an eleventh embodiment, this invention relates to a method of identifying an isolated polynucleotide that encodes a delta-9 fatty acid desaturase comprising the steps of: determining an amino acid sequence of the polypeptide encoded by the isolated DNA; determining if the amino acid sequence comprises at least two amino acid sequences selected from the group consisting of HSMPPEK corresponding to amino acids 67-73 of SEQ ID NO:2, LPLLKPVE corresponding to amino acids 89-96 of SEQ ID NO:2, EYFVVLVGDM corresponding to amino acids 132-141 of SEQ ID NO:2, EKTV corresponding to amino acids 205-208 of SEQ ID NO:2, GMDPGT corresponding to amino acids 215-220 of SEQ ID NO:2, NNPYLGFVYTSFQERAT corresponding to amino acids 222-238 of SEQ ID NO:2, VLAR corresponding to amino acids 256-259 of SEQ ID NO:2, RIVE corresponding to amino acids 277-280 of SEQ ID NO:2, ITMPAHL corresponding to amino acids 302-308 of SEQ ID NO:2, or DFVCGLA corresponding to amino acids 364-370 of SEQ ID NO:2.

In an twelfth embodiment, this invention relates to a method of identifying an isolated polynucleotide that encodes a delta-9 fatty acid desaturase comprising the steps of: determining the polypeptide sequence by one of the aforementioned methods; determining that the amino acid sequence of the polypeptide does not contain at least one of the following amino acid sequences KEIPDDYFVVLVGDMITEEALPTYQTMLNT corresponding to positions 116-145 of SEQ ID NO:23; or DYADILEFLVGRWK corresponding to positions 324-337 of SEQ ID NO:23.

In an thirteenth embodiment, this invention relates to a method of altering the level of expression of a diverged delta-9 fatty acid desaturase in a host cell comprising: (a) transforming a host cell with a chimeric construct of the present invention; and (b) growing the transformed host cell under conditions that are suitable for expression of the chimeric construct wherein expression of the chimeric construct results in production of altered levels of the a diverged delta-9 fatty acid desaturase in the transformed host cell.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1 shows a comparison of the amino acid stearoyl-ACP desaturase sequences of the soybean enzyme [SEQ ID NO:2], corn [SEQ ID NOs:10 and 12], rice [SEQ ID NOs:14 and 16], to the lupine [gi 4704824, SEQ ID NO:17], jojoba [gi 267036, SEQ ID NO:20], Arabidopsis [gi 6957724, SEQ ID NO:21], flax [gi 3355632, SEQ ID NO:22], and to the soybean stearoyl-ACP desaturase [SEQ ID NO:23] found in U.S. Pat. No. 5,760,206.

Table 2 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 2

Diverged Delta-9 Fatty Acid Desaturase

| Protein | Clone Designation | SEQ ID NO: (Nucleotide) | SEQ ID NO: (Amino Acid) |
|---|---|---|---|
| Soybean [*Glycine max*] | se6.pk0026.a8 | 1 | 2 |
| Corn [*Zea mays*] | cbn10.pk0061.a3 | 3 | 4 |
| Corn [*Zea mays*] | contig of: cen7f.pk001.k12 cpd1c.pk012.n9 cpd1c.pk014.l18 p0103.ciaad81r p0106.cjlpm88r | 5 | 6 |
| Rice [*Oryza sativa*] | rds1c.pk007.g19 | 7 | 8 |
| Corn [*Zea mays*] | cbn10.pk0061.a3:fis | 9 | 10 |
| Corn [*Zea mays*] | cpd1c.pk014.l18:fis | 11 | 12 |
| Rice [*Oryza sativa*] | rds1c.pk007.g19:fis | 13 | 14 |
| Rice [*Oryza sativa*] | rsl1n.pk008.j18:fis | 15 | 16 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

A new diverged class of delta-9 steroyl desaturases are disclosed herein. These desaturases were obtained from soybean, corn, and rice and are less than 60% identical to the previously characterized class. This new diverged class of delta-9 steroyl desaturases still performs the substantially identical biochemical function in plants as the previously characterized class. In addition, evidence is presented to show that the new class of desaturases may play a more important role in regulating fatty acid synthesis than the previous class.

The terms "diverged delta-9 fatty acid desaturase", "diverged delta-9 stearoyl desaturase", or "diverged delta-9 desaturase" are used interchangeably herein and include, but are not limited to, all plant delta-9 stearoyl desaturases that are less than 60% identical to the previously characterized delta-9 stearoyl desaturases (PCT Publication Nos. WO 91/13972 and WO 91/18985). This new diverged class of delta-9 steroyl desaturases still performs the substantially identical biochemical function in plants as the previously characterized class, namely the introduction of a double bond between carbon atoms 9 and 10 of stearoyl-ACP to form oleoyl-ACP.

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 30 contiguous nucleotides, preferably at least one of 40 contiguous nucleotides, most preferably one of at least 60 contiguous nucleotides derived from SEQ ID NO:1, 3, 5, 7, 9, 11, 13, or 15, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "host" refers to any organism, or cell thereof, whether human or non-human into which a recombinant construct can be stably or transiently introduced in order to alter gene expression in the host.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. In a preferred embodiment, it has been found that suitable nucleic sequences and their reverse complement can be used to alter the expression of any homologous, endogensous RNA which is in proximity to the suitable nucleic acid and its reverse complement. This is described in greater detail in Applicant's Assignee's co-pending provisional application having Application No. 60/213961 filed Jun. 23, 2000, the disclosure of which is hereby incorporated by reference.

In addition, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 30 (preferably at least one of 40, most preferably at least one of 60) contiguous nucleotides derived from a nucleotide sequence selected from the group consisting of SEQ ID NO:1, 3, 5, 7, 9, 11, 13, or 15, and the complement of such nucleotide sequences may be used in methods of selecting an isolated polynucleotide that affects the expression of a diverged delta-9 stearoyl desaturase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino'acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed, using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

It should be appreciated by one skilled in the art that genes encoding delta-9 desaturases can be identified in a number of ways. Conserved sequence motifs such as HSMPPEK corresponding to amino acids 67-73 of SEQ ID NO:2, LPLLKPVE corresponding to amino acids 89-96 of SEQ ID NO:2, EYFV-VLVGDM corresponding to amino acids 132-141 of SEQ ID NO:2, EKTV corresponding to amino acids 205-208 of SEQ ID NO:2, GMDPGT corresponding to amino acids 215-220 of SEQ ID NO:2, NNPYLGFVYTSFQERAT corresponding to amino acids 222-238 of SEQ ID NO:2, VLAR corresponding to amino acids 256-259 of SEQ ID NO:2, RIVE corresponding to amino acids 277-280 of SEQ ID NO:2, ITMPAHL corresponding to amino acids 302-308 of SEQ ID NO:2, or DFVCGLA corresponding to amino acids 364-370 of SEQ ID NO:2, can be used once several members of a diverged class are identified (as is the case in the present invention). In addition one can use hybridization, sequencing, and electronic alignment to aid the identification of gene candidates. These approaches can be coupled to assay of the polypeptide activity in bacterial, yeast, or plant host cells. Stable transgenic plants would provide a preferred method of determining the identity of a nucleic acid sequence encoding a delta-9 desaturase.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding-polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from postranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single Polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Overexpression" refers to the produciton of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, the disclosure of which is hereby incorporated by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" as used herein refers to a host cell which either does not express a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100: 1627-1632).

The present invention describes a nucleic acid fragment that encodes a diverged delta-9 fatty acid desaturase. This enzyme catalyzes the introduction of a double bond between carbon atoms 9 and 10 of stearoyl-ACP to form oleoyl-ACP. It can also convert stearoyl-CoA into oleoyl-CoA, albeit with reduced efficiency. Transfer of the nucleic acid fragment of the invention, or a part thereof that encodes a functional enzyme, with suitable regulatory sequences into a living cell will result in the production or over-production of stearoyl-ACP desaturase, which in the presence of an appropriate electron donor, such as ferredoxin, may result in an increased level of unsaturation in cellular lipids, including oil, in tissues when the enzyme is absent or rate-limiting.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945, 050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 400 amino acids having at least 80% identity based on the Clustal method of alignment when compared to a polypeptide selected from the group consisting of SEQ ID NO:2, 4, 6, 8, 10, 12, 14, or 16, or (b) a second nucleotide sequence comprising the complement of the first nucleotide sequence.

Preferably, the first nucleotide sequence comprises a nucleic acid sequence selected from the group consisting of SEQ ID NO:1, 3, 5, 7, 9, 11, 13, or 15, that codes for the polypeptide selected from the group consisting of SEQ ID NO:2, 4, 6, 8, 10, 12, 14, or 16.

Nucleic acid fragments encoding at least a portion of several diverged delta-9 fatty acid desaturases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other diverged delta-9 stearoyl desaturases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 30 (preferably one of at least 40, most preferably one of at least 60) contiguous nucleotides derived from a nucleotide sequence selected from the group consisting of SEQ ID NO:1, 3, 5, 7, 9, 11, 13, or 15 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a diverged delta-9 stearoyl desaturase polypeptide, preferably a substantial portion of a plant diverged delta-9 stearoyl desaturase polypeptide, comprising the steps of: synthesizing an oligonucleotide primer comprising a nucleotide sequence of at least one of 30 (preferably at least one of 40, most preferably at least one of 60) contiguous nucleotides derived from a nucleotide sequence selected from the group consisting of SEQ ID NO:1, 3, 5, 7, 9, 11, 13, or 15, and the complement of such nucleotide sequences; and amplifying a nucleic acid fragment (preferably a cDNA inserted in a cloning vector) using the oligonucleotide primer. The amplified nucleic acid fragment preferably will encode a portion of a diverged delta-9 stearoyl desaturase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric constructs of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of mono-, poly- and unsaturated fatty acids in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

The terms "chimeric construct", "recombinant construct", "expression construct" and "recombinant expression construct" are used interchangeably herein. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric construct designed for co-suppression of the instant polypeptide can be constructed by linking a gene or gene fragment encoding that polypeptide to plant promoter sequences. Alternatively, a chimeric construct designed to express antisense RNA for all or part of the instant nucleic acid fragment can be constructed by linking the gene or gene fragment in reverse orientation to plant promoter sequences. Either the co-suppression or antisense chimeric constructs could be introduced into plants via transformation wherein expression of the corresponding endogenous genes are reduced or eliminated. In a preferred embodiment, it has been found that suitable nucleic sequences and their reverse complement can be used to alter the expression of any homologous, endogenous RNA which is in proximity to the suitable nucleic acid and its reverse complement. This is described in greater detail in Applicant's Assignee's co-pending provisional application having Application No. 60/213961 filed Jun. 23, 2000, the disclosure of which is hereby incorporated by reference.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 400 amino acids that has at least 80% identity based on the Clustal method of alignment when compared to a polypeptide selected from the group consisting of SEQ ID NO:2, 4, 6, 8, 10, 12, 14, or 16.

The instant polypeptides (or portions thereof may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to make a chimeric construct for production of the instant polypeptides. This chimeric construct could then be introduced into appropriate microorganisms via transformation to provide high level expression of the encoded diverged delta-9 fatty acid desaturase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. in: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

Methods for assaying delta-9 fatty acid desaturase activities in *E. coli* have been previously described (U.S. Pat. Nos. 5,443,974 and 5,760,206). Fatty acid analysis of oil samples is performed by gas chromatography. Briefly, fatty acid (FA) determination was done from a total of 300-400 mg of tissue lyophilized for 24 hours. The tissue was then ground using a FastPrep mill (Bio101) at 4.5 speed and 20 seconds in the presence of 0.5 ml of 2.5% Sulfuric Acid +97.5% Methanol and Heptadecanoic acid (17:0, stock 10 mg/ml in Tuloene) as an external standard. Thereafter, another 0.5 ml 2.5% Sulfuric Acid+97.5% Methanol was used to wash each tube and incubate in 95° C. for 1 hour for transesterification. The tubes were removed from the water bath and allowed to cool down to room temperature. FAs were extracted in one volume of heptane:$H_2O$ (1:1) and cleared by centrifugation. The supernatant (50 ul) containing the fatty acid methyl esters were loaded into a Hewlett Packard 6890 gas chromatograph fitted with a 30 m×0.32 mm Omegawax column and the separated peaks were analyzed and characterized.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various soybean, corn, and rice tissues were prepared. The characteristics of the libraries are described below.

TABLE 3 cDNA Libraries from Soybean, Corn, and Rice

| Library | Description | Clone |
|---------|-------------|-------|
| se6 | Soybean Embryo, 26 Days After Flowering | se6.pk0026.a8 |
| cbn10 | Corn Developing Kernel (Embryo and Endosperm); 10 Days After Pollination | cbn10.pk0061.a3<br>cbn10.pk0061.a3:fis |
| cpd1c | Corn (*Zea mays* L.) pooled BMS treated with chemicals related to protein kinases | cpd1c.pk014.l18<br>cpd1c.pk014.l18:fis |
| rds1c | Rice (*Oryza sativa*, YM) developing seeds 1 | rds1c.pk007.g19<br>rds1c.pk007.g19:fis |
| rsl1n | Rice (*Oryza sativa*, YM) 15 day old seedling normalized | rsl1n.pk008.j18:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding a diverged delta-9 fatty acid desaturase were identified by conducting BLAST (Basic Local Alignment Search Tool; Altschul et al. (1993) *J. Mol. Biol.* 215:403-410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding a Diverged Delta-9, or Stearoyl-ACP, Desaturase The BLASTX search using the EST sequences from clones listed in Table 3 revealed similarity of the polypeptides encoded by the cDNAs to a diverged delta-9, or stearoyl-ACP, desaturase from lupine (*Lupinus luteus*), cucumber (*Cucumis sativus*), Arabidopsis (*Arabidopsis thaliana*), jojoba (*Simmondsia chinensis*), Arabidopsis (*Arabidopsis thaliana*), and flax (*Linum usitatissimum*) (NCBI General Identifier Nos. gi 4704824, gi 417820, gi 7523660, gi 267036, gi 6957724, and gi 3355632 respectively). Shown in Table 4 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 4

BLAST Results for Sequences Encoding Polypeptides Homologous to a Diverged Delta-9, or Stearoyl-ACP, Desaturase

| Clone | Status | BLAST pLog | gi # |
|---|---|---|---|
| se6.pk0026.a8 | CGS | 254.00 | 4704824 |
| cbn10.pk0061.a3 | EST | 2.52 | 4704824 |
| cpd1c.pk014.l18 | contig | 107.00 | 417820 |
| rds1c.pk007.g19 | EST | 33.04 | 7523660 |
| cbn10.pk0061.a3:fis | CGS | 113.00 | 267036 |
| cpd1c.pk014.l18:fis | CGS | 149.00 | 4704824 |
| rds1c.pk007.g19:fis | FIS | 60.52 | 6957724 |
| rsl1n.pk008.j18:fis | CGS | 147.00 | 3355632 |

FIG. 1 presents an alignment of the amino acid sequences set forth in SEQ ID NO:2, 10, 12, 14, and 16, and the lupine, jojoba, *Arabidopsis*, and flax sequences (SEQ ID NO:17, 20, 21, and 22) and the original soybean delta-9 desaturase presented in U.S. Pat. No. 5,760,206 (SEQ ID NO:23). The data in Table 5 represents a calculation of the percent identity of the amino acid sequences set forth in SEQ ID NOs:2, 4, 6, 8, 10, 12, 14, and 16, and the lupine, cucumber, *Arabidopsis*, jojoba, *Arabidopsis*, and flax sequences (SEQ ID NOs:17, 18, 19, 20, 21, and 22; NCBI General Identifier Nos. gi 4704824, gi 417820, gi 7523660, gi 267036, gi 6957724, and gi 3355632 respectively).

TABLE 5

Percent Identity of Polypeptides Homologous to a Diverged Delta-9, or Stearoyl-ACP, Desaturase

| SEQ ID NO. | Percent Identity | gi # |
|---|---|---|
| 2 | 77.6% | 4704824 |
| 4 | 16.4% | 4704824 |
| 6 | 62.3% | 417820 |
| 8 | 59.5% | 7523660 |
| 10 | 49.2% | 267036 |
| 12 | 64.2% | 4704824 |
| 14 | 50.2% | 6957724 |
| 16 | 64.0% | 3355632 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1 GAP PENALTY=3, WINDOW=5 and DIAGONALS SAVED=5. Sequence alignments and BLAST scores and probabilities indicate that the nucleic acid fragments comprising the instant cDNA clones encode a substantial portion of a diverged delta-9, or stearoyl-ACP, desaturase. Confirmation of the biochemical identity of each clone is accomplished according to methods well known to those skilled in the art (U.S. Pat. No. 5,760,206).

Example 4

Expression of Chimeric Constructs in Monocot Cells

A chimeric construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI- NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric construct encoding, in the 5' to 3' direction, the maize 27 kD zein promoter, a cDNA fragment encoding the instant polypeptides, and the 10 kD zein 3' region.

The chimeric construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgeric callus by first transferring clusters of tissue to N6 medium supplemented with 0.2 mg per liter of 2,4-D. After two weeks the tissue can be transferred to regeneration medium (Fromm et al., (1990) *Bio/Technology* 8:833-839).

Example 5

Expression of Chimeric Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-α-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Transformation Of Somatic Soybean Embryo Cultures

Soybean embryogenic suspension cultures were maintained in 35 ml liquid media (SB55 or SBP6) on a rotary shaker, 150 rpm, at 28° C. with mixed fluorescent and incandescent lights on a 16:8 h day/night schedule. Cultures were subcultured every four weeks by inoculating approximately 35 mg of tissue into 35 ml of liquid medium.

TABLE 6

| Stock Solutions (g/L): MS Sulfate 100X Stock | |
|---|---|
| $MgSO_4 \, 7H_2O$ | 37.0 |
| $MnSO_4 \, H_2O$ | 1.69 |
| $ZnSO_4 \, 7H_2O$ | 0.86 |
| $CuSO_4 \, 5H_2O$ | 0.0025 |

TABLE 6-continued

MS Halides 100X Stock

| | |
|---|---|
| CaCl$_2$ 2H$_2$O | 44.0 |
| KI | 0.083 |
| CoCl$_2$ 6H$_2$O | 0.00125 |
| KH$_2$PO$_4$ | 17.0 |
| H$_3$BO$_3$ | 0.62 |
| Na$_2$MoO$_4$ 2H$_2$O | 0.025 |

MS FeEDTA 100X Stock

| | |
|---|---|
| Na$_2$EDTA | 3.724 |
| FeSO$_4$ 7H$_2$O | 2.784 |

B5 Vitamin Stock 10 g m-inositol
100 mg nicotinic acid
100 mg pyridoxine HCl
1 g thiamine SB55 (per Liter, pH 5.7)

10 mL each MS stocks
1 mL B5 Vitamin stock
0.8 g NH$_4$NO$_3$
3.033 g KNO$_3$
1 mL 2,4-D (10 mg/mL stock)
60 g sucrose
0.667 g asparagine

SBP6 same as SB55 except 0.5 mL 2,4-D

SB103 (per Liter, pH 5.7)

1X MS Salts
6% maltose
750 mg MgCl$_2$
0.2% Gelrite

SB71-1 (per Liter, pH 5.7)

1X B5 salts
1 ml B5 vitamin stock
3% sucrose
750 mg MgCl$_2$
0.2% Gelrite

Soybean embryogenic suspension cultures were transformed with pTC3 by the method of particle gun bombardment (Kline et al. (1987) *Nature* 327:70). A DuPont Biolistic PDS1000/HE instrument (helium retrofit) was used for these transformations.

To 50 ml of a 60 mg/ml 1 mm gold particle suspension was added (in order); 5 µl DNA(1 µg/µl), 20 µl spermidine (0.1 M), and 50 µl CaCl$_2$ (2.5 M). The particle preparation was agitated for 3 min, spun in a microfuge for 10 sec and the supernatant removed. The DNA-coated particles were then washed once in 400 µl 70% ethanol and re suspended in 40 µl of anhydrous ethanol. The DNA/particle suspension was sonicated three times for 1 sec each. Five µl of the DNA-coated gold particles were then loaded on each macro carrier disk.

Approximately 300-400 mg of a four week old suspension culture was placed in an empty 60×15 mm petri dish and the residual liquid removed from the tissue with a pipette. For each transformation experiment, approximately 5-10 plates of tissue were normally bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/ml hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as independent transformation event. These suspensions can then be maintained as suspensions of embryos clustered in an immature developmental stage through subculture or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in their fatty acid compositions (Example 8). Co-suppression of Fad2 results in a reduction of polyunsaturated fatty acids and an increase in oleic acid content. Co-suppression of the delta-9 desaturases of the instant invention result in an increase in the accumulation of stearic acid (18:0 fatty acid).

Example 8

The Phenotype of Transgenic Soybean Somatic Embryos Is Predictive of Seed Phenotypes From Resultant Regenerated Plants Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α' subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis somatic soybean embryo system behaves very similarly to maturing zygotic soybean embryos in vivo, and is therefore a good and rapid model system for analyzing the phenotypic effects of modifying the expression of genes in the fatty acid biosynthesis pathway.

Most importantly, the model system is also predictive of the fatty acid composition of seeds from plants derived from transgenic embryos. This is illustrated with two different antisense constructs in two different types of experiment that were constructed following the protocols set forth in the PCT Publication Nos. WO 93/11245 and WO 94/11516. Liquid culture globular embryos were transformed with a chimeric gene comprising a soybean microsomal $\Delta^{15}$ desaturase as described in PCT Publication No. WO 93/11245 which was published on Jun. 10, 1993, the disclosure of which is hereby incorporated by reference (experiment 1,) or a soybean microsomal $\Delta^{12}$ desaturase as described in PCT Publication No. WO 94/11516 which was published on May 26, 1994, the disclosure of which is hereby incorporated by reference (experiment 2). Both gene constructs were introduced in antisense orientation under the control of a seed-specific promoter (β-conglycinin promoter) and gave rise to mature embryos. The fatty acid content of mature somatic embryos from lines transformed with vector only (control) and the vector containing the antisense chimeric genes as well as of seeds of plants regenerated from them was determined.

One set of embryos from each line was analyzed for fatty acid content and another set of embryos from that same line was regenerated into plants. Fatty acid analysis of single embryos was determined either by direct trans-esterification of individual seeds in 0.5 mL of methanolic $H_2SO_4$ (2.5%) or by hexane extraction of bulk seed samples followed by trans-esterification of an aliquot in 0.8 mL of 1% sodium methoxide in methanol. Fatty acid methyl esters were extracted from the methanolic solutions into hexane after the addition of an equal volume of water. In all cases, if there was a reduced 18:3 content in a transgenic embryo line when compared to an untransformed control, then a corresponding reduction in 18:3 content was also observed in the segregating seeds of the plant derived from that transformed line (Table 7).

TABLE 7

Percent 18:3 Content Of Embryos and Seeds of Control and $\Delta^{15}$ Antisense Construct Transgenic Soybean Lines

| Transformant Line | Embryo Average (SD, n = 10) | Seed Average (SD, n = 10) |
|---|---|---|
| Control | 12.1 (2.6) | 8.9 (0.8) |
| $\Delta^{15}$ antisense, line 1 | 5.6 (1.2) | 4.3 (1.6) |
| $\Delta^{15}$ antisense, line 2 | 8.9 (2.2) | 2.5 (1.8) |
| $\Delta^{15}$ antisense, line 3 | 7.3 (1.1) | 4.9 (1.9) |
| $\Delta^{15}$ antisense, line 4 | 7.0 (1.9) | 2.4 (1.7) |
| $\Delta^{15}$ antisense, line 5 | 8.5 (1.9) | 4.5 (2.2) |
| $\Delta^{15}$ antisense, line 6 | 7.6 (1.6) | 4.6 (1.6) |

*[Seeds which were segregating with wild-type phenotype and without a copy of the transgene are not included in these averages]

In addition, different lines containing the same antisense construct, were used for fatty acid analysis in somatic embryos and for regeneration into plants. About 55% of the transformed embryo lines showed an increased 18:1 content when compared with control lines (Table 8). Soybean seeds, of plants regenerated from different somatic embryo lines containing the same antisense construct, had a similar frequency (53%) of high oleate transformants as the somatic embryos (Table 8). On occasion, an embryo line may be chimeric. That is, 10-70% of the embryos in a line may not contain the transgene. The remaining embryos that do contain the transgene, have been found in all cases to be clonal. In such a case, plants with both wild type and transgenic phenotypes may be regenerated from a single, transgenic line, even if most of the embryos analyzed from that line had a transgenic phenotype. An example of this is shown in Table 9, in which, of 5 plants regenerated from a single embryo line, 3 have a high oleic phenotype and two were wild type. In most cases, all the plants regenerated from a single transgenic line will have seeds containing the transgene. Thus, it was concluded that an altered fatty acid phenotype observed in a transgenic, mature somatic embryo line is predictive of an altered fatty acid composition of seeds of plants derived from that line.

TABLE 8

Oleate Levels in Somatic Embryos and Seeds of Regenerated Soybeans Transformed With, or Without, $\Delta^{12}$ Desaturase Antisense Construct

| | # of Vector Lines | # of Lines with High 18:1 | Average* % 18:1 |
|---|---|---|---|
| Somatic embryos: | | | |
| Control | 19 | 0 | 12.0 |
| $\Delta^{12}$ antisense | 20 | 11 | 35.3 |
| Seeds of regenerated plants: | | | |
| Control | 6 | 0 | 18.2 |
| $\Delta^{12}$ antisense | 17 | 9 | 44.4 |

*average 18:1 of transgenics is the average of all embryos or seeds transformed with the $\Delta^{12}$ antisense construct in which at least one embryo or seed from that line had an 18:1 content greater than 2 standard deviations from the control value (12.0 in embryos, 18.2 in seeds). The control average is the average of embryos or seeds which do not contain any transgenic DNA but have been treated in an identical manner to the transgenics.

TABLE 9

Analysis of Seeds From Five Independent Plants Segregating From Plant Line 4

| Plant # | Average seed 18:1% | Highest seed 18:1% |
|---|---|---|
| 1 | 18.0 | 26.3 |
| 2 | 33.6 | 72.1 |
| 7 | 13.6 | 21.2 |
| 9 | 32.9 | 57.3 |
| 11 | 24.5 | 41.7 |

Mean of 15-20 seeds from 5 different plants regenerated from a single embryo line. Only plants # 2, 9 and 11 have seeds with a high 18:1 phenotype.

Example 9

Suppression in Soybean of Fad2 By ELVISLIVES Complementary Region

Cosuppression of plant genes is covered in a U.S. provisional patent application 60/213961 filed on Jun. 23, 2000, and nationally filed in the USPTO as application Ser. No. 09/887,194 on Jun. 22, 2001, the contents of which are hereby incorporated by reference. Constructs have now been made which have "synthetic complementary regions" (SCR). Since complementary regions from Fad 2 can successfully suppress a thioesterase target, and a Cer3 complementary region can suppress Fad2, it was deduced that it may be possible to use any complementary sequence to reduce the expression of a target. In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and 133 plasmids use the Kti promoter, both of these promoters exhibit strong tissue specific expression in the seeds of soybean. pKS106 uses a 3' termination region from the phaseolin gene, and pKS124 and 133 use a Kti 3' termination region. pKS106 and 124 have single copies of the 36 nucleotide EagI-ELVISLIVES sequence surrounding a NotI site (the amino acids given in parentheses are back-translated from the complementary strand): SEQ ID NO:24.

```
EagI    E   L   V   I   S   L   I   V   E   S   NotI
CGGCCG GAG CTG GTC ATC TCG CTC ATC GTC GAG TCG
GCGGCCGC (S) (E) (V) (I) (L) (S) (I) (V) (L) (E) EagI
CGA CTC GAC GAT GAG CGA GAT GAC CAG CTC CGGCCG
``` pKS133 has 2x copies of ELVISLIVES surrounding the NotI site:

SEQ ID NO: 25

```
EagI   E  L  V  I  S  L  I  V  E  S     EagI    E  L  V  I  S
cggccggagctggtcatctcgctcatcgtcgagtcg gcggccg gagctggtcatctcg L  I  V  E  S    NotI    (S)  (E  (V) (I) (L) (S) (I) (V) (L)
(E)

EagI
ctcatcgtcgagtcg gcggccgc cgactcgacgatgagcgagatgaccagctc cggccgc (S) (E) (V) (I) (L) (S) (I) (V) (L) (E)   EagI
cgactcgacgatgagcgagatgaccagctc cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths are also under evaluation. It is believed that certain combinations of target lengths and complementary region lengths will give optimum suppression of the target, although preliminary results would indicate that the suppression phenomenon works well over a wide range of sizes and sequences. It is also believed that the lengths and ratios providing optimum suppression may vary somewhat given different target sequences and/or complementary regions.

The efficiency of Fad2 suppression using 1×EL (pKS132) was compared to Fad2 suppression using the 2×EL (pKS136) construct. Hygromycin resistant lines of soybean embryos were isolated from independent transformation experiments with pKS132 and pKS136. Out of 98 lines containing pKS132, 69% displayed the high oleic phenotype. Out of 54 lines containing pKS136, 70% displayed the high oleic acid phenotype. Thus, both 1× and 2×EL constructs efficiently suppressed the Fad2 target gene.

Example 10

Suppression the Diverged Delta-9 Desaturase Results in High Stearate Phenotypes

The two soybean delta-9 desaturase genes previously identified, designated pDS 1 and 2 (U.S. Pat. Nos. 5,443,974 and 5,760,206) share a high degree of homology to other known delta-9 desaturase genes such as castor and safflower (U.S. Pat. No. 5,723,595). The genes of the present invention have less than 65% amino acid sequence identity to these previously described plant delta-9 desaturase polypeptides. All of the soybean delta-9 desaturase genes were placed into *E. coli* and shown to have delta-9 desaturase activity. To test if the three genes had comparable activities in vivo, transgenic plants were constructed.

Delta-9 desaturase enzymes introduce a double bond into stearic acid to form oleic acid. Inhibition of this activity should result in an increase in stearic acid content and a correlative reduction in unsaturated fatty acids in the oil. An antisense construct of pDS1 (pKS6) was made using the entire coding region in reverse orientation inserted into the SmaI/XbaI site of pCST2 (PCT Publication No. WO 94/11516, published May 26, 1994) behind a beta-conglycinin promoter. A cosuppression construct was made (pRB1) where the HindIII fragment containing the beta-conglycinin promoter and the phaseolin 3' terminator from pAW35 (U.S. Pat. No. 5,952,544) was inserted into the HindIII site of pML18 (PCT Publication No. WO 94/11516, published May 26, 1994) to form pBS19. The coding region of pDS1 was inserted into the Not I site of pBS19 to form pRB1. Finally, a cosuppression construct was made using pDS3 (pBS68, SEQ ID NO:26) by placing approximately 950 basepairs of pDS3 in the sense orientation between 2×EL complementary regions as described in Example 9 (the pDS region of pBS68 is from positions 6054-6611 linked to 1-411 of SEQ ID NO:26). The construct has a Kti3 promoter (position 3260-5348 of SEQ ID NO:26), a Kti3 terminator (position 523-725 of SEQ ID NO:26), and hygromycin selection (position 1920-880 of SEQ ID NO:26). Soybean transformations were done as previously described (Example 7), and soybean embryo tissue was assayed. As outlined in Example 8, soybean embryo tissue is representative of seed tissues when seed specific promoters such as beta-conglycinin or Kti3 are used.

The results shown in Table 10 demonstrate that pDS3 is as good, or better, than pDS1 at increasing stearic acid content in oils when cosuppressed in plant tissue. On average there is a 7.4-fold increase in 18:0 content with pDS3 (pBS68) versus 4.5 for the cosuppressed pDS1. Antisense or cosuppression gave similar results. The tranformants that showed the highest levels of stearic acid are shown in the "best" columns.

TABLE 10

18:0 Content of Wild Type and Transgenic High 18:0 Soybean Somatic Embryos

|  | wild type (s.d.) | high 18:0 (s.d.) | fold increase | best 18:0 | best fold increase | # of high 18:0 events |
|---|---|---|---|---|---|---|
| pKS6 | 3.6 (0.8) | 16.7 (5.6) | 4.6x | 34.5 | 9.6x | 40 |
| pRB1 | 3.4 (0.5) | 15.4 (3.7) | 4.5x | 20.6 | 6.1x | 10 |
| pBS68 | 2.5 (0.8) | 18.6 (6.9) | 7.4x | 29.1 | 11.6x | 10 |

These results confirm that the diverged delta-9 desaturase sequences do encode functional enzymes. Furthermore, pDS3 may be the dominant activity found in soybeans. The conserved sequence elements KEIPDDYFVVLVGDMI-TEEALPTYQTMLNT corresponding to positions 116-145 of SEQ ID NO:23; and DYADILEFLVGRWK corresponding to positions 324-337 of SEQ ID NO:23 from the Thompson patent (U.S. Pat. No. 5,723,595) that are claimed to be indicative of delta-9 desaturases are not conserved in the diverged sequences of the instant invention. Therefore, the sequences of the instant invention define a new functional class of plant delta-9 desaturase genes.

What is claimed is:

1. An isolated polynucleotide comprising:
   (a) a nucleotide sequence encoding a polypeptide having delta-9 fatty acid desaturase activity that has at least 80% identity based on the Clustal method of alignment with pairwise alignment default parameters of KTUPLE=1, GAP PENALTY=3, WINDOW=5 and DIAGONALS SAVED=5, when compared to a polypeptide selected from the group consisting of SEQ ID NO:2; or
   (b) the complement of (a).

2. An isolated polynucleotide comprising:
   (a) a nucleotide sequence encoding a polypeptide having delta-9 fatty acid desaturase activity that has at least 85% identity based on the Clustal method of alignment with pairwise alignment default parameters of KTUPLE=1, GAP PENALTY=3, WINDOW=5 and DIAGONALS SAVED=5, when compared to a polypeptide selected from the group consisting of SEQ ID NO:2; or
   (b) the complement of (a).

3. An isolated polynucleotide comprising:
   (a) a nucleotide sequence encoding a polypeptide having delta-9 fatty acid desaturase activity that has at least 90% identity based on the Clustal method of alignment with pairwise alignment default parameters of KTUPLE=1, GAP PENALTY=3, WINDOW=5 and DIAGONALS SAVED=5, when compared to SEQ ID NO:2; or
   (b) the complement of (a).

4. An isolated polynucleotide comprising:
   (a) a nucleotide sequence encoding a polypeptide having delta-9 fatty acid desaturase activity that has at least 95% identity based on the Clustal method of alignment with pairwise alignment default parameters of KTUPLE=1, GAP PENALTY=3, WINDOW=5 and DIAGONALS SAVED=5, when compared to a SEQ ID NO:2; or
   (b) the complement of (a).

5. The isolated polynucleotide of any of claims 1-4, wherein the nucleotide sequence comprises the nucleic acid sequence of SEQ ID NO:1.

6. A chimeric construct comprising the isolated polynucleotide of any of claims 1-4 operably linked to at least one suitable regulatory sequence.

7. A chimeric construct comprising the isolated polynucleotide of claim 5 operably linked to at least one suitable regulatory sequence.

8. A host cell comprising the chimeric construct of claim 6.

9. A host cell comprising the chimeric construct of claim 7.

* * * * *

SEQUENCE LISTING

```
<160> NUMBER OF SEQ ID NOS: 26

<210> SEQ ID NO 1
<211> LENGTH: 1560
<212> TYPE: DNA
<213> ORGANISM: Glycine max

<400> SEQUENCE: 1
gaggcgttgg atctggcact cgttttgctg tggctgctct ctgaaactga aagcgaagca      60
gcagccactg aaaagcagaa aacaaaggga aagaacaagc ttagccatgc tgagtattat     120
attcaaggaa ttcgtcaagt acaatagaca cgtaatcaaa accatgcaga tacgaacctg     180
ccactccatc accacccaaa cccttccaca acttccgtgt tcttctagaa aagcccacca     240
ccgccacctt cttccgccgt taaacgctgc ggtttccgcg cgccgttca aagcccggaa      300 ggcccactca atgcctccag aaaagaaaga aattttcaag tccttggagg gatgggcctc     360
ggagtgggtc ctaccgctgc tgaagcccgt ggagcaatgc tggcagccac aaaacttcct     420
ccctgacccc tcccttccgc atgaagagtt cagccatcag gtgaaggagc ttcgcgaacg     480
cactaaagag ttacctgatg agtactttgt ggtgctggtg ggtgatatgg tcaccgagga     540
cgcgcttccc acttaccaga ccatgatcaa caaccttgat ggagtgaaag atgacagcgg     600
cacgagcccg agcccgtggg ccgtgtggac ccgggcctgg accgccgagg aaaacagaca     660
cggggatctg ctcagaactt atttgtatct ctctgggagg gttgacatgg ctaaggtcga     720
aaagaccgta cattacctca tttcagctgg catggaccct gggacagaca caacccata      780 tttggggttt gtgtacacgt cattccaaga gcgagcaaca tttgtggcgc acgggaacac     840
ggctcggctc gcgaaggagg gcgggggatcc agtgctggcg cgcctatgcg ggaccatcgc     900
agcggacgag aagcggcacg agaacgcgta ctcaagaatc gtggagaagc ttctggaagt     960
ggaccccacc ggggcaatgg tggccatagg aacatgatg gagaagaaga tcacgatgcc     1020
ggcgcacctt atgtacgatg gggatgaccc caggctattc gagcactact ccgctgtggc     1080
gcagcgcata ggcgtgtaca ccgccaacga ctacgcagac atcttggagt ttctcgttga     1140
acggtggaga ttggagaagc ttgaaggatt gatggctgag gggaagcggg cgcaggattt     1200
cgtgtgtggg ttggcgccga ggattaggag gttgcaagaa cgcgctgatg agcgagcgcg     1260
taagatgaag aagcatcatg gcgttaagtt cagttggatt ttcaataaag aattgctttt     1320
gtgaaatttc agttaagact taagagataa gagatagagg tcaacgtgag tcaacaggtt     1380
tttggctttg tgactatttt gagttttttgt ttgtaggtgg catttttagt acgaataatg     1440
aacaatttaa catggattgc gtgtaatgga cattgttgga tccatggttg ttgttctggt     1500
```

```
ggatacacaa ccagtaggac ttttttgttg taacgtttgg cttgcatatt agcttagctt    1560
```

<210> SEQ ID NO 2
<211> LENGTH: 405
<212> TYPE: PRT
<213> ORGANISM: Glycine max

<400> SEQUENCE: 2

| Met | Leu | Ser | Ile | Ile | Phe | Lys | Glu | Phe | Val | Lys | Tyr | Asn | Arg | His | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ile Lys Thr Met Gln Ile Arg Thr Cys His Ser Ile Thr Thr Gln Thr
             20                  25                  30

Leu Pro Gln Leu Pro Cys Ser Ser Arg Lys Ala His Arg His Leu
         35                  40                  45

Leu Pro Pro Leu Asn Ala Ala Val Ser Ala Ala Pro Phe Lys Ala Arg
 50                  55                  60

Lys Ala His Ser Met Pro Pro Glu Lys Glu Ile Phe Lys Ser Leu
 65                  70                  75                  80

Glu Gly Trp Ala Ser Glu Trp Val Leu Pro Leu Leu Lys Pro Val Glu
                 85                  90                  95

Gln Cys Trp Gln Pro Gln Asn Phe Leu Pro Asp Pro Ser Leu Pro His
                100                 105                 110

Glu Glu Phe Ser His Gln Val Lys Glu Leu Arg Glu Arg Thr Lys Glu
            115                 120                 125

Leu Pro Asp Glu Tyr Phe Val Val Leu Val Gly Asp Met Val Thr Glu
130                 135                 140

Asp Ala Leu Pro Thr Tyr Gln Thr Met Ile Asn Asn Leu Asp Gly Val
145                 150                 155                 160

Lys Asp Asp Ser Gly Thr Ser Pro Ser Pro Trp Ala Val Trp Thr Arg
                165                 170                 175

Ala Trp Thr Ala Glu Glu Asn Arg His Gly Asp Leu Leu Arg Thr Tyr
            180                 185                 190

Leu Tyr Leu Ser Gly Arg Val Asp Met ala Lys Val Glu Lys Thr Val
        195                 200                 205

His Tyr Leu Ile Ser Ala Gly Met Asp Pro Gly Thr Asp Asn Asn Pro
    210                 215                 220

Tyr Leu Gly Phe Val Tyr Thr Ser Phe Gln Glu Arg Ala Thr Phe Val
225                 230                 235                 240

Ala His Gly Asn Thr Ala Arg Leu Ala Lys Glu Gly Gly Asp Pro Val
                245                 250                 255

Leu Ala Arg Leu Cys Gly Thr Ile Ala Ala Asp Glu Lys Arg His Glu
            260                 265                 270

Asn Ala Tyr Ser Arg Ile Val Glu Lys Leu Leu Glu Val Asp Pro Thr
        275                 280                 285

Gly Ala Met Val Ala Ile Gly Asn Met Met Glu Lys Lys Ile Thr Met
290                 295                 300

Pro Ala His Leu Met Tyr Asp Gly Asp Pro Arg Leu Phe Glu His
305                 310                 315                 320

Tyr Ser Ala Val Ala Gln Arg Ile Gly Val Tyr Thr Ala Asn Asp Tyr
                325                 330                 335

Ala Asp Ile Leu Glu Phe Leu Val Glu Arg Trp Arg Leu Glu Lys Leu
            340                 345                 350

Glu Gly Leu Met ala Glu Gly Lys Arg Ala Gln Asp Phe Val Cys Gly
        355                 360                 365

Leu Ala Pro Arg Ile Arg Arg Leu Gln Glu Arg Ala Asp Glu Arg Ala
    370                 375                 380

Arg Lys Met Lys Lys His His Gly Val Lys Phe Ser Trp Ile Phe Asn
385                 390                 395                 400

Lys Glu Leu Leu Leu
            405

<210> SEQ ID NO 3
<211> LENGTH: 563
<212> TYPE: DNA
<213> ORGANISM: Zea mays
<220> FEATURE:
<221> NAME/KEY: unsure
<222> LOCATION: (308)
<220> FEATURE:
<221> NAME/KEY: unsure
<222> LOCATION: (458)
<220> FEATURE:
<221> NAME/KEY: unsure
<222> LOCATION: (483)
<220> FEATURE:
<221> NAME/KEY: unsure
<222> LOCATION: (494)
<220> FEATURE:
<221> NAME/KEY: unsure
<222> LOCATION: (519)
<220> FEATURE:
<221> NAME/KEY: unsure
<222> LOCATION: (521)
<220> FEATURE:
<221> NAME/KEY: unsure
<222> LOCATION: (545)
<220> FEATURE:
<221> NAME/KEY: unsure
<222> LOCATION: (550)
<220> FEATURE:
<221> NAME/KEY: unsure
<222> LOCATION: (557)

<400> SEQUENCE: 3
agcgaccaaa cccgggcacc tcgtctagct cgccttccat ttcgtccctt cctattcata      60
ctaccttcta cgagtttgag cagccatggc ggcaacaaca ccactgcttg ctgtggctgg     120
acatggagta tcctacaaac cagcaaatgc taaagacagc tactactgct tcaaatttgc     180
atcatcggca agaacaagag tcaccctccc acagatcatc cactggaggt gcaggagcag     240
tcatagcagc acggggacca cgaccatggc cgtccctgtc ctcaagcggc gggagaagca     300
ggacgaanag caggaatgga tggggtacct ggccccggag aagctggagg tgctagcaca     360
cctggagccg tgggcggagg cgcacgtgct gccgctgctg aagcccgcgg aggagggtgg     420
aaccgtcgga catctccgga ccggcgcgct ggcgacangg ctcacaccgt gccgcaactc     480
gcnccggggg caantgccga cccactgggt gctggtggna natatacgag gaggctgcca     540
gtcanagcgn ccaacgntca ggg                                             563

<210> SEQ ID NO 4
<211> LENGTH: 110
<212> TYPE: PRT
<213> ORGANISM: Zea mays
<220> FEATURE:
<221> NAME/KEY: UNSURE
<222> LOCATION: (75)

<400> SEQUENCE: 4

Met ala Ala Thr Thr Pro Leu Leu Ala Val Ala Gly His Gly Val Ser
  1               5                  10                  15

Tyr Lys Pro Ala Asn Ala Lys Asp Ser Tyr Tyr Cys Phe Lys Phe Ala

```
                    20                  25                  30
Ser Ser Ala Arg Thr Arg Val Thr Leu Pro Gln Ile Ile His Trp Arg
            35                  40                  45

Cys Arg Ser Ser His Ser Ser Thr Gly Thr Thr Thr Met ala Val Pro
        50                  55                  60

Val Leu Lys Arg Arg Glu Lys Gln Asp Glu Xaa Gln Glu Trp Met Gly
65                  70                  75                  80

Tyr Leu Ala Pro Glu Lys Leu Glu Val Leu Ala His Leu Glu Pro Trp
                85                  90                  95

Ala Glu Ala His Val Leu Pro Leu Leu Lys Pro Ala Glu Glu
            100                 105                 110

<210> SEQ ID NO 5
<211> LENGTH: 880
<212> TYPE: DNA
<213> ORGANISM: Zea mays

<400> SEQUENCE: 5
cgtcggcacg agcggcacga gctcgtgccg cgtccactcc acagtcaccc accgccgcct      60
cctccagcgt ccggcccgta cgccgcgcag ccaacccagc gggcacgatg caggcccacg     120
gcatcgccat ccgcgcccgc gggcggtgg cggcgacgca ggcccccgcg cgccgacggc      180
aatgccgcgt gtctgcggcg gcggtcggcg cgcccgccgc gcgcgcccgc gtgacgcact     240
cgatgccgcc ggagaaggcg gaggtgttcc gctcgctgga gggctgggcg gcgcggtcgc     300
tgctgccgct gctcaagccc gtggaggagt gctggcagcc ggcggacttc ctcccggact     360
cctcgtccga gatgttcggg cacgaggtcc gcgagctgcg cgcccgcgcc gcggggctcc     420
ccgacgagta cttcgtcgtg ctcgtgggcg acatggtcac ggaagaggcg ctgcccacgt     480
accagaccat gatcaacacg ctcgacggcg tccgcgacga gaccggcgcc agcaactgcc     540
cctgggcggt ctggacgcgc gcctggaccc cgaggagaa ccgccacggc gacatcctcg      600
gcaagtacat gtacctatcc ggccgcgtcg acatgcgcat ggtcgagaag accgtccagt     660
acctcatcgg ctccggcatg gatcccggaa cggagaacaa cccgtacctg gcttcgtgt      720
acacgagctt ccaggagcgc gcgacggccg tctcgcacgg caacaccgcg cggctcccca     780
gggcgcacgg ggacgacttc ttggcgcgcg cctgcgggac caaccgccgc caacaagaaa     840
cgaaacaaaa cgggttaagg ggcatcctcc aagaagttgg                           880

<210> SEQ ID NO 6
<211> LENGTH: 257
<212> TYPE: PRT
<213> ORGANISM: Zea mays

<400> SEQUENCE: 6

Met Gln Ala His Gly Ile Ala Ile Arg Ala Arg Gly Pro Val Ala Ala
1               5                   10                  15

Thr Gln Ala Pro Ala Arg Arg Arg Gln Cys Arg Val Ser Ala Ala Ala
            20                  25                  30

Val Gly Ala Pro Ala Ala Arg Ala Arg Val Thr His Ser Met Pro Pro
        35                  40                  45

Glu Lys Ala Glu Val Phe Arg Ser Leu Glu Gly Trp Ala Ala Arg Ser
    50                  55                  60

Leu Leu Pro Leu Leu Lys Pro Val Glu Glu Cys Trp Gln Pro Ala Asp
65                  70                  75                  80

Phe Leu Pro Asp Ser Ser Ser Glu Met Phe Gly His Glu Val Arg Glu
```

-continued

```
                              85                  90                  95
Leu Arg Ala Arg Ala Ala Gly Leu Pro Asp Glu Tyr Phe Val Val Leu
            100                 105                 110

Val Gly Asp Met Val Thr Glu Glu Ala Leu Pro Thr Tyr Gln Thr Met
            115                 120                 125

Ile Asn Thr Leu Asp Gly Val Arg Asp Glu Thr Gly Ala Ser Asn Cys
            130                 135                 140

Pro Trp Ala Val Trp Thr Arg Ala Trp Thr Ala Glu Glu Asn Arg His
145                 150                 155                 160

Gly Asp Ile Leu Gly Lys Tyr Met Tyr Leu Ser Gly Arg Val Asp Met
                165                 170                 175

Arg Met Val Glu Lys Thr Val Gln Tyr Leu Ile Gly Ser Gly Met Asp
            180                 185                 190

Pro Gly Thr Glu Asn Asn Pro Tyr Leu Gly Phe Val Tyr Thr Ser Phe
            195                 200                 205

Gln Glu Arg Ala Thr Ala Val Ser His Gly Asn Thr Ala Arg Leu Pro
            210                 215                 220

Arg Ala His Gly Asp Asp Phe Leu Ala Arg Ala Cys Gly Thr Asn Arg
225                 230                 235                 240

Arg Gln Gln Glu Thr Lys Gln Asn Gly Leu Arg Gly Ile Leu Gln Glu
                245                 250                 255

Val
257
```

```
<210> SEQ ID NO 7
<211> LENGTH: 463
<212> TYPE: DNA
<213> ORGANISM: Oryza sativa
<220> FEATURE:
<221> NAME/KEY: unsure
<222> LOCATION: (334)
<220> FEATURE:
<221> NAME/KEY: unsure
<222> LOCATION: (350)
<220> FEATURE:
<221> NAME/KEY: unsure
<222> LOCATION: (358)
<220> FEATURE:
<221> NAME/KEY: unsure
<222> LOCATION: (431)
<220> FEATURE:
<221> NAME/KEY: unsure
<222> LOCATION: (434)
<220> FEATURE:
<221> NAME/KEY: unsure
<222> LOCATION: (436)
<220> FEATURE:
<221> NAME/KEY: unsure
<222> LOCATION: (444)
<220> FEATURE:
<221> NAME/KEY: unsure
<222> LOCATION: (452)
<220> FEATURE:
<221> NAME/KEY: unsure
<222> LOCATION: (463)

<400> SEQUENCE: 7
gtacctctcc ggccgcttcg acatggccga ggtggagcgc gccgtgcacc gcctcatccg      60
ctccggcatg gccgtcgacc cgccgtgcag cccgtaccac gccttcgtct acacggcgtt    120
ccaggagcgc gccacggcgg tcgcccacgg caacacggcg cggctggtcg gcgcgcgagg    180
gcacggcgac gccgccctcg cccgcgtctg cggcaccgtc gccgccgacg agaagcggca    240
cgaggccgcc tacacccgca tcgtctccag gctcctcgag gccgacccgg acgccggcgt    300
```

```
gcgcgcggtg gcgcgcatgc tacggcgagg ggtncccaa tgccgaactn ggcccatnct    360
ccgacggccg ccgcgacgac ctctaacgcc tgcgtcggtg tcccctccgc cgaagcaggg    420
ccgggacgta nagngnggtc ggantaactg gntcaatccg tcn                     463
```

<210> SEQ ID NO 8
<211> LENGTH: 111
<212> TYPE: PRT
<213> ORGANISM: Oryza sativa

<400> SEQUENCE: 8

```
Tyr Leu Ser Gly Arg Phe Asp Met ala Glu Val Glu Arg Ala Val His
 1               5                  10                  15

Arg Leu Ile Arg Ser Gly Met ala Val Asp Pro Pro Cys Ser Pro Tyr
             20                  25                  30

His Ala Phe Val Tyr Thr Ala Phe Gln Glu Arg Ala Thr Ala Val Ala
         35                  40                  45

His Gly Asn Thr Ala Arg Leu Val Gly Ala Arg Gly His Gly Asp Ala
     50                  55                  60

Ala Leu Ala Arg Val Cys Gly Thr Val Ala Ala Asp Glu Lys Arg His
 65                  70                  75                  80

Glu Ala Ala Tyr Thr Arg Ile Val Ser Arg Leu Leu Glu Ala Asp Pro
                 85                  90                  95

Asp Ala Gly Val Arg Ala Val Ala Arg Met Leu Arg Arg Gly Val
             100                 105                 110
```

<210> SEQ ID NO 9
<211> LENGTH: 1483
<212> TYPE: DNA
<213> ORGANISM: Zea mays

<400> SEQUENCE: 9

```
gcacgagagc gaccaaaccc gggcacctcg tctagctcgc cttccatttc gtcccttcct     60
attcatacta ccttctacga gtttgagcag ccatggcggc aacaacacca ctgcttgctg    120
tggctggaca tggagtatcc tacaaaccag caaatgctaa agacagctac tactgcttca    180
aatttgcatc atcggcaaga acaagagtca ccctcccaca gatcatccac tggaggtgca    240
ggagcagtca tagcagcacg gggaccacga ccatggccgt ccctgtcctc aagcggcggg    300
agaagcagga cgaagagcag gaatggatgg ggtacctggc cccggagaag ctggaggtgc    360
tagcacacct ggagccgtgg gcggaggcgc acgtgctgcc gctgctgaag cccgcggagg    420
aggcgtggca gccgtcggac atgctcccgg accggcggc gctgggcgac gagggcttcc    480
acgacgcgtg ccgcgagctc cgcgcgcggg cggccagcgt gcccgacgcc cacctggtgt    540
gcctggtggg caacatgatc actgaggagg ccctgcccac gtaccagagc gtgcctaacc    600
gcttcgaggc cgtgcgcgac ctcaccggcc ccgactccac cgcctgggcg cgctggatcc    660
gcggctggtc cgccgaggag aaccgccacg gcgacgccct cagccactac atgtacctct    720
cgggccgcgt cgacatgcgc caggtcgacc gcaccgtgca ccgcctcatc gcctccggca    780
tggccatgaa cgccgccagg agccctacc acggcttcat ctacgtcgct ttccaggagc    840
gcgccaccgc catctcgcac ggcaacatgg cgcggcacgt cggcgcgcac ggcgaccacg    900
tgctcgcccg cgtatgcggc ccatcatgg ccgacgagaa cgccacgag accgcataca    960 cccgcatcgt cgccaagctc ttcgaggtcg accggacgc ggccgtgcgc gcgctcggct   1020
acatgatgcg ccaccggatc accatgccgg cagcgctcat gaccgacggc cgcgacgccc   1080
```

```
acctctacgc ccactacgcc gccgccgcgc agcagaccgg cgtgtacact gcgtctgact   1140
accgaagcat cctggagcac ctcatacggc agtggcgcgt ggaggagctc gcggcggggc   1200
tctccggcga ggggaggcgc gcgcgggact acgtgtgcgg gctgccgcac aagatccgga   1260
ggatggagga aaggcccat gacagggcgg cccagaccca gaaaaagccc acgtctgtcc   1320
cgtttagctg gatcttcgat agatccgtca atgtcgtgat tccgtaattt tcctcaaaaa   1380
aaattgagaa tcaggttatg cttagaggtg cattcactgt tgtgtggatt atccttgcaa   1440
taaaaaaaca acgccttgcg ggtgaaaaaa aaaaaaaaaa aaa   1483
```

<210> SEQ ID NO 10
<211> LENGTH: 424
<212> TYPE: PRT
<213> ORGANISM: Zea mays

<400> SEQUENCE: 10

```
Met Ala Ala Thr Thr Pro Leu Leu Ala Val Ala Gly His Gly Val Ser
  1               5                  10                  15

Tyr Lys Pro Ala Asn Ala Lys Asp Ser Tyr Tyr Cys Phe Lys Phe Ala
             20                  25                  30

Ser Ser Ala Arg Thr Arg Val Thr Leu Pro Gln Ile Ile His Trp Arg
         35                  40                  45

Cys Arg Ser Ser His Ser Ser Thr Gly Thr Thr Met Ala Val Pro
     50                  55                  60

Val Leu Lys Arg Glu Lys Gln Asp Glu Glu Gln Glu Trp Met Gly
 65                  70                  75                  80

Tyr Leu Ala Pro Glu Lys Leu Glu Val Leu Ala His Leu Glu Pro Trp
             85                  90                  95

Ala Glu Ala His Val Leu Pro Leu Leu Lys Pro Ala Glu Glu Ala Trp
            100                 105                 110

Gln Pro Ser Asp Met Leu Pro Asp Pro Ala Ala Leu Gly Asp Glu Gly
        115                 120                 125

Phe His Asp Ala Cys Arg Glu Leu Arg Ala Arg Ala Ala Ser Val Pro
    130                 135                 140

Asp Ala His Leu Val Cys Leu Val Gly Asn Met Ile Thr Glu Glu Ala
145                 150                 155                 160

Leu Pro Thr Tyr Gln Ser Val Pro Asn Arg Phe Glu Ala Val Arg Asp
            165                 170                 175

Leu Thr Gly Ala Asp Ser Thr Ala Trp Ala Arg Trp Ile Arg Gly Trp
        180                 185                 190

Ser Ala Glu Glu Asn Arg His Gly Asp Ala Leu Ser His Tyr Met Tyr
    195                 200                 205

Leu Ser Gly Arg Val Asp Met Arg Gln Val Ala Arg Thr Val His Arg
    210                 215                 220

Leu Ile Ala Ser Gly Met Ala Met Asn Ala Ala Arg Ser Pro Tyr His
225                 230                 235                 240

Gly Phe Ile Tyr Val Ala Phe Gln Glu Arg Ala Thr Ala Ile Ser His
            245                 250                 255

Gly Asn Met Ala Arg His Val Gly Ala His Gly Asp His Val Leu Ala
        260                 265                 270

Arg Val Cys Gly Ala Ile Met Ala Asp Glu Lys Arg His Glu Thr Ala
    275                 280                 285

Tyr Thr Arg Ile Val Ala Lys Leu Phe Glu Val Asp Pro Asp Ala Ala
    290                 295                 300
```

```
Val Arg Ala Leu Gly Tyr Met Met Arg His Arg Ile Thr Met Pro Ala
305                 310                 315                 320

Ala Leu Met Thr Asp Gly Arg Asp Ala His Leu Tyr Ala His Tyr Ala
            325                 330                 335

Ala Ala Ala Gln Gln Thr Gly Val Tyr Thr Ala Ser Asp Tyr Arg Ser
            340                 345                 350

Ile Leu Glu His Leu Ile Arg Gln Trp Arg Val Glu Glu Leu Ala Ala
            355                 360                 365

Gly Leu Ser Gly Glu Gly Arg Arg Ala Arg Asp Tyr Val Cys Gly Leu
370                 375                 380

Pro His Lys Ile Arg Met Glu Glu Lys Ala His Asp Arg Ala Ala
385                 390                 395                 400

Gln Thr Gln Lys Lys Pro Thr Ser Val Pro Phe Ser Trp Ile Phe Asp
                405                 410                 415

Arg Ser Val Asn Val Val Ile Pro
            420

<210> SEQ ID NO 11
<211> LENGTH: 1415
<212> TYPE: DNA
<213> ORGANISM: Zea mays

<400> SEQUENCE: 11
gcacgagcgg cacgagcggc acgagctcgt gccgcgtcca ctccacagtc acccaccgcc      60
gcctcctcca gcgtccggcc cgtacgccgc gcagccaacc cagcgggcac gatgcaggcc     120
cacggcatcg ccatccgcgc ccgcgggccg gtggcggcga gcaggcccc cgcgcgccga     180 cggcaatgcc gcgtgtctgc ggcggcggtc ggcgcgcccg ccgcgcgcgc ccgcgtgacg     240
cactcgatgc cgccggagaa ggcggaggtg ttccgctcgc tggagggctg ggcggcgcgg     300
tcgctgctgc tctgctcaa gcccgtggag gagtgctggc agccggcgga cttcctcccg     360
gactcctcgt ccgagatgtt cgggcacgag gtccgcgagc tgcgcgcccg cgccgcgggg     420
ctccccgacg agtacttcgt cgtgctcgtg ggcgacatgg tcacggaaga ggcgctgccc     480
acgtaccaga ccatgatcaa cacgctcgac ggcgtccgcg acgagaccgg cgccagcaac     540
tgcccctggg cggtctggac gcgcgcctgg accgccgagg agaaccgcca cggcgacatc     600
ctcggcaagt acatgtacct atccggccgc gtcgacatgc gcatggtcga agaccgtc      660 cagtacctca tcggctccgg catggatccc ggaacggaga acaacccgta cctgggcttc     720
gtgtacacga gcttccagga gcgcgcgacg gccgtctcgc acggcaacac cgcgcggctc     780
gccagggcgc acggggacga cgtcctggcg cgcgcctgcg gcaccatcgc cgccgacgag     840
aagcggcacg agacggcgta cgggcgcatc gtcgagcagc tgctgcagct ggaccccgag     900
ggcgccgtgc tcgccgtcgc ggacatgatg cgcaagcgga tcaccatgcc cgcgcacctc     960
atgcacgacg gccgcgacat ggacctgttc gagcacttcg ccgccgtcgc ccagcgcctc    1020
ggcgtgtaca ccgcccggga ctacgcggac atcgtcgagt ccttgtcaa gcggtggaag    1080 ctggagacac tggagagcgg gctctccggc gagggccgca gggccaggga cttcgtctgc    1140
gggctcgcgc cgaggatgcg ccgggccgcg gagcgcgccg aggacagggc caagaaggac    1200
gagcccagga tggtcaagtt cagctggatc tttgatagg aagccgttgt ttaggcactt    1260
gttgctaact gtgatatgtg ctcagatcat gtcgctagct gtcagtgtct ttgtcacatt    1320
gtgtttatgt gtttgaaatg ccgtaagagt gttttttttcc tgctattatc acaaaattct    1380
```
gcagaaatat atgttctaaa aaaaaaaaaa aaaaa         1415

<210> SEQ ID NO 12
<211> LENGTH: 380
<212> TYPE: PRT
<213> ORGANISM: Zea mays

<400> SEQUENCE: 12

```
Met Gln Ala His Gly Ile Ala Ile Arg Ala Arg Gly Pro Val Ala Ala
 1               5                  10                  15

Thr Gln Ala Pro Ala Arg Arg Gln Cys Arg Val Ser Ala Ala Ala
            20                  25                  30

Val Gly Ala Pro Ala Ala Arg Ala Arg Val Thr His Ser Met Pro Pro
        35                  40                  45

Glu Lys Ala Glu Val Phe Arg Ser Leu Glu Gly Trp Ala Ala Arg Ser
    50                  55                  60

Leu Leu Pro Leu Leu Lys Pro Val Glu Glu Cys Trp Gln Pro Ala Asp
 65                  70                  75                  80

Phe Leu Pro Asp Ser Ser Glu Met Phe Gly His Glu Val Arg Glu
                85                  90                  95

Leu Arg Ala Arg Ala Ala Gly Leu Pro Asp Glu Tyr Phe Val Val Leu
            100                 105                 110

Val Gly Asp Met Val Thr Glu Glu Ala Leu Pro Thr Tyr Gln Thr Met
        115                 120                 125

Ile Asn Thr Leu Asp Gly Val Arg Asp Glu Thr Gly Ala Ser Asn Cys
    130                 135                 140

Pro Trp Ala Val Trp Thr Arg Ala Trp Thr Ala Glu Glu Asn Arg His
145                 150                 155                 160

Gly Asp Ile Leu Gly Lys Tyr Met Tyr Leu Ser Gly Arg Val Asp Met
                165                 170                 175

Arg Met Val Glu Lys Thr Val Gln Tyr Leu Ile Gly Ser Gly Met Asp
            180                 185                 190

Pro Gly Thr Glu Asn Asn Pro Tyr Leu Gly Phe Val Tyr Thr Ser Phe
        195                 200                 205

Gln Glu Arg Ala Thr Ala Val Ser His Gly Asn Thr Ala Arg Leu Ala
    210                 215                 220

Arg Ala His Gly Asp Asp Val Leu Ala Arg Ala Cys Gly Thr Ile Ala
225                 230                 235                 240

Ala Asp Glu Lys Arg His Glu Thr Ala Tyr Gly Arg Ile Val Glu Gln
                245                 250                 255

Leu Leu Gln Leu Asp Pro Glu Gly Ala Val Leu Ala Val Ala Asp Met
            260                 265                 270

Met Arg Lys Arg Ile Thr Met Pro Ala His Leu Met His Asp Gly Arg
        275                 280                 285

Asp Met Asp Leu Phe Glu His Phe Ala Ala Val Ala Gln Arg Leu Gly
    290                 295                 300

Val Tyr Thr Ala Arg Asp Tyr Ala Asp Ile Val Glu Phe Leu Val Lys
305                 310                 315                 320

Arg Trp Lys Leu Glu Thr Leu Glu Ser Gly Leu Ser Gly Glu Gly Arg
                325                 330                 335

Arg Ala Arg Asp Phe Val Cys Gly Leu Ala Pro Arg Met Arg Arg Ala
            340                 345                 350

Ala Glu Arg Ala Glu Asp Arg Ala Lys Lys Asp Glu Pro Arg Met Val
        355                 360                 365
```

-continued

Lys Phe Ser Trp Ile Phe Asp Arg Glu Ala Val Val
    370             375             380

<210> SEQ ID NO 13
<211> LENGTH: 773
<212> TYPE: DNA
<213> ORGANISM: Oryza sativa

<400> SEQUENCE: 13
gcaccaggta cctctccggc cgcttcgaca tggccgaggt ggagcgcgcc gtgcaccgcc      60
tcatccgctc cggcatggcc gtcgacccgc cgtgcagccc gtaccacgcc ttcgtctaca     120
cggcgttcca ggagcgcgcc acggcggtcg cccacggcaa cacggcgcgg ctggtcggcg     180
cgcgagggca cggcgacgcc gccctcgccc gcgtctgcgg caccgtcgcc gccgacgaga     240
agcggcacga ggccgcctac acccgcatcg tctccaggct cctcgaggcc gacccggacg     300
ccggcgtgcg cgcggtggcg cgcatgctac ggcgaggggt cgccatgccg acctcgccca     360
tctccgacgg ccgccgcgac gacctctacg cctgcgtcgt gtccctcgcc gagcaggccg     420
ggacgtacac ggtgtcggac tactgctcca tcgtcgagca cctggtgcgg gagtggcgcg     480
tggaggagct cgcggcgggg ctctccggcg aagggcggcg cgcgcgggac tacgtgtgcg     540
agctgccgca agatccgg aggatgaagg agaaggccca tgagagggcg gtcaaggccc      600
agaagaagcc catcagcatc ccgattaatt ggatatttga taggcacgtc agtgtcatgc     660
tgccctaatt taattaaaaa aaaaaaaaaa aaaaaaaaaa aaaaaaaaaa aaaaaaaaa      720
aaaaaaaaaa aaaaaaaaaa aaaaaaaaaa aaaaaaaaaa aaaaaaaaaa aaa           773

<210> SEQ ID NO 14
<211> LENGTH: 219
<212> TYPE: PRT
<213> ORGANISM: Oryza sativa

<400> SEQUENCE: 14

Tyr Leu Ser Gly Arg Phe Asp Met Ala Glu Val Glu Arg Ala Val His
  1               5                  10                  15

Arg Leu Ile Arg Ser Gly Met Ala Val Asp Pro Pro Cys Ser Pro Tyr
             20                  25                  30

His Ala Phe Val Tyr Thr Ala Phe Gln Glu Arg Ala Thr Ala Val Ala
         35                  40                  45

His Gly Asn Thr Ala Arg Leu Val Gly Ala Arg Gly His Gly Asp Ala
     50                  55                  60

Ala Leu Ala Arg Val Cys Gly Thr Val Ala Ala Asp Glu Lys Arg His
 65                  70                  75                  80

Glu Ala Ala Tyr Thr Arg Ile Val Ser Arg Leu Leu Glu Ala Asp Pro
                 85                  90                  95

Asp Ala Gly Val Arg Ala Val Ala Arg Met Leu Arg Arg Gly Val Ala
            100                 105                 110

Met Pro Thr Ser Pro Ile Ser Asp Gly Arg Arg Asp Asp Leu Tyr Ala
        115                 120                 125

Cys Val Val Ser Leu Ala Glu Gln Ala Gly Thr Tyr Thr Val Ser Asp
    130                 135                 140

Tyr Cys Ser Ile Val Glu His Leu Val Arg Glu Trp Arg Val Glu Glu
145                 150                 155                 160

Leu Ala Ala Gly Leu Ser Gly Glu Gly Arg Arg Ala Arg Asp Tyr Val
                165                 170                 175

Cys Glu Leu Pro Gln Lys Ile Arg Arg Met Lys Glu Lys Ala His Glu

```
                        180                 185                 190
Arg Ala Val Lys Ala Gln Lys Lys Pro Ile Ser Ile Pro Ile Asn Trp
        195                 200                 205

Ile Phe Asp Arg His Val Ser Val Met Leu Pro
    210                 215

<210> SEQ ID NO 15
<211> LENGTH: 1318
<212> TYPE: DNA
<213> ORGANISM: Oryza sativa

<400> SEQUENCE: 15
gcacgagaac tagctactgt agttgactga cagtgatagt ggcagtcatg caggtcgtgg      60
gaaccgtgcg tgtcagtggc tgcggcgcgg tggtggcgcc ctcgcgccgg cagtgccgcg     120
tgtccgcggc ggtgctgacg gccgcggaga cggcgacggc gacgcggcgc cgcgtgacgc     180
actcgatgcc gccggagaag gcggaggtgt tccggtcgct ggaagggtgg gcgaggtcgt     240
cgctgctgcc gctgctcaag cccgtggagg agtgctggca gccgacggac ttcctgccgg     300
actcgtcgtc ggagatgttc gagcaccagg tccacgagct ccgcgcgcgc gccgcggggc     360
tccccgacga gtacttcgtc gtgctggtcg gggacatgat taccgaggag cgctgccga      420 cgtaccagac catgatcaac acgctcgacg cgtccgcga cgagaccggc gccagcgcct      480
gcccctgggc cgtctggacg cgcacctgga ccgccgagga gaaccgccac ggcgacatcc     540
tcggcaagta catgtacctc tccggccgcg tcgacatgcg catggtcgag aagaccgtcc     600
agtacctcat cggctccggc atggatccgg ggacggagaa caacccgtac ctggggttcg     660
tgtacaccag cttccaggag cgcgcgacgg ccgtgtcgca cgggaacacg gcgcgcctcg     720
ccagggcgca cggggacgac gtcctggcgc gcacctgcgg caccatcgcc gccgacgaga     780
agcggcacga gacggcgtac gggcgcatcg tggagcagct gctgcggctc gacccggacg     840
gcgccatgct cgccatcgcc gacatgatgc acaagcggat caccatgccc gcgcacctca     900
tgcacgacgg ccgcgacatg aacctgttcg accacttcgc cgccgtggcg cagcgcctca     960
acgtctacac cgcgcgcgac tacgccgaca tcgtcgagtt cctcgtcaag cggtggaagc    1020
tggagaccct ggagactggg ctctccggcg agggccggag ggcccgggac ttcgtgtgcg    1080
ggctcgcgaa gaggatgcgg cgggccgcgg agcgggctga ggacagggct aagaaggatg    1140
agcagaggaa ggtcaagttc agctggatct atgataggga agtgattgtc tagtttaact    1200
tgtcttggtt gaattctgaa ttcccagtcc tagatgatca tgccatttcg ttatcatctc    1260
tgttcttgtg ttctctttgc aatgcagtaa attggtaata aaaaaaaaaa aaaaaaa      1318

<210> SEQ ID NO 16
<211> LENGTH: 381
<212> TYPE: PRT
<213> ORGANISM: Oryza sativa

<400> SEQUENCE: 16

Met Gln Val Val Gly Thr Val Arg Val Ser Gly Cys Gly Ala Val Val
  1               5                  10                  15

Ala Pro Ser Arg Arg Gln Cys Arg Val Ser Ala Ala Val Leu Thr Ala
                 20                  25                  30

Ala Glu Thr Ala Thr Ala Thr Arg Arg Arg Val Thr His Ser Met Pro
             35                  40                  45

Pro Glu Lys Ala Glu Val Phe Arg Ser Leu Glu Gly Trp Ala Arg Ser
         50                  55                  60
```

Ser Leu Leu Pro Leu Leu Lys Pro Val Glu Glu Cys Trp Gln Pro Thr
65                  70                  75                  80

Asp Phe Leu Pro Asp Ser Ser Glu Met Phe Glu His Gln Val His
            85                  90                  95

Glu Leu Arg Ala Arg Ala Ala Gly Leu Pro Asp Glu Tyr Phe Val Val
            100                 105                 110

Leu Val Gly Asp Met Ile Thr Glu Glu Ala Leu Pro Thr Tyr Gln Thr
                115                 120                 125

Met Ile Asn Thr Leu Asp Gly Val Arg Asp Glu Thr Gly Ala Ser Ala
        130                 135                 140

Cys Pro Trp Ala Val Trp Thr Arg Thr Trp Thr Ala Glu Glu Asn Arg
145                 150                 155                 160

His Gly Asp Ile Leu Gly Lys Tyr Met Tyr Leu Ser Gly Arg Val Asp
                165                 170                 175

Met Arg Met Val Glu Lys Thr Val Gln Tyr Leu Ile Gly Ser Gly Met
            180                 185                 190

Asp Pro Gly Thr Glu Asn Asn Pro Tyr Leu Gly Phe Val Tyr Thr Ser
        195                 200                 205

Phe Gln Glu Arg Ala Thr Ala Val Ser His Gly Asn Thr Ala Arg Leu
210                 215                 220

Ala Arg Ala His Gly Asp Asp Val Leu Ala Arg Thr Cys Gly Thr Ile
225                 230                 235                 240

Ala Ala Asp Glu Lys Arg His Glu Thr Ala Tyr Gly Arg Ile Val Glu
                245                 250                 255

Gln Leu Leu Arg Leu Asp Pro Asp Gly Ala Met Leu Ala Ile Ala Asp
            260                 265                 270

Met Met His Lys Arg Ile Thr Met Pro Ala His Leu Met His Asp Gly
        275                 280                 285

Arg Asp Met Asn Leu Phe Asp His Phe Ala Ala Val Ala Gln Arg Leu
290                 295                 300

Asn Val Tyr Thr Ala Arg Asp Tyr Ala Asp Ile Val Glu Phe Leu Val
305                 310                 315                 320

Lys Arg Trp Lys Leu Glu Thr Leu Glu Thr Gly Leu Ser Gly Glu Gly
            325                 330                 335

Arg Arg Ala Arg Asp Phe Val Cys Gly Leu Ala Lys Arg Met Arg Arg
        340                 345                 350

Ala Ala Glu Arg Ala Glu Asp Arg Ala Lys Lys Asp Glu Gln Arg Lys
    355                 360                 365

Val Lys Phe Ser Trp Ile Tyr Asp Arg Glu Val Ile Val
    370                 375                 380

<210> SEQ ID NO 17
<211> LENGTH: 384
<212> TYPE: PRT
<213> ORGANISM: Lupinus luteus

<400> SEQUENCE: 17

Met Gln Ile Gln Thr Cys Tyr Ser Ile Arg Ile Gln Ile Leu Pro Leu
1               5                   10                  15

Pro Trp Ala Arg Arg Thr Gly Arg His Lys Met Leu Pro Pro Ile Ala
            20                  25                  30

Ala Ile Ser Ala Thr Pro Pro Ser Leu Lys Ser Pro Lys Thr His Ser
        35                  40                  45

Met Pro Pro Glu Lys Ile Glu Ile Phe Lys Ser Leu Glu Ser Trp Ala

```
            50                  55                  60
Ser Gln Ser Val Leu Pro Leu Lys Pro Val Glu Gln Cys Trp Gln
 65                  70                  75                  80

Pro Gln Glu Phe Val Pro Asp Ser Ser Leu Pro Phe Gly Asp Phe Thr
                 85                  90                  95

Asp Gln Val Lys Ala Leu Arg Asp Arg Thr Ala Glu Leu Pro Glu Glu
                100                 105                 110

Tyr Phe Val Leu Val Gly Asp Met Ile Thr Glu Asp Ala Leu Pro
                115                 120                 125

Thr Tyr Gln Ser Met Ile Asn Asn Leu Asp Gly Val Arg Asp Glu Thr
130                 135                 140

Gly Ser Ser Pro Ser Pro Trp Ala Leu Trp Thr Arg Ala Trp Thr Ala
145                 150                 155                 160

Glu Glu Lys Arg His Gly Asp Leu Leu Arg Thr Tyr Leu Tyr Leu Ser
                165                 170                 175

Gly Arg Val Asp Met Lys Lys Ile Glu Lys Thr Val Gln Tyr Leu Ile
                180                 185                 190

Gly Ser Gly Met Asp Pro Gly Thr Glu Asn Asn Pro Tyr Leu Gly Phe
                195                 200                 205

Val Tyr Thr Ser Phe Gln Glu Arg Ala Thr Phe Val Ser His Gly Asn
                210                 215                 220

Thr Ala Arg Leu Ala Lys Glu Gly Gly Asp Pro Val Leu Ala Arg Ile
225                 230                 235                 240

Cys Gly Thr Ile Ala Ala Asp Glu Lys Arg His Glu Asn Ala Tyr Ser
                245                 250                 255

Arg Ile Val Glu Lys Leu Leu Glu Leu Asp Pro Thr Gly Ala Met Val
                260                 265                 270

Ala Ile Gly Asp Met Met Gln Lys Lys Ile Thr Met Pro Ala His Leu
                275                 280                 285

Met Tyr Asp Gly Glu Asp Pro Lys Leu Phe Asp His Phe Ser Ala Val
                290                 295                 300

Ala Gln Arg Met Gly Val Tyr Thr Ala Asn Asp Tyr Ala Asp Ile Leu
305                 310                 315                 320

Glu Phe Leu Ile Gly Arg Trp Arg Leu Glu Lys Val Gln Asp Leu Lys
                325                 330                 335

Asp Glu Gly Lys Lys Ala Gln Asp Phe Val Cys Gly Leu Ala Pro Arg
                340                 345                 350

Ile Arg Arg Leu Gln Glu Arg Ala Asp Glu Arg Ala Arg Lys Met Lys
                355                 360                 365

Pro His Ala Val Lys Phe Ser Trp Ile Phe Asn Lys Glu Ile Ile Leu
                370                 375                 380

<210> SEQ ID NO 18
<211> LENGTH: 396
<212> TYPE: PRT
<213> ORGANISM: Cucumis sativus

<400> SEQUENCE: 18

Met Ala Leu Lys Phe His Pro Leu Thr Ser Gln Ser Pro Lys Leu Pro
 1               5                  10                  15

Ser Phe Arg Met Pro Gln Leu Ala Ser Leu Arg Ser Pro Lys Phe Val
                20                  25                  30

Met Ala Ser Thr Leu Arg Ser Thr Ser Arg Glu Val Glu Thr Leu Lys
                35                  40                  45
```

-continued

```
Lys Pro Phe Met Pro Pro Arg Glu Val His Leu Gln Val Thr His Ser
     50                  55                  60

Met Pro Pro Gln Lys Met Glu Ile Phe Lys Ser Leu Glu Asp Trp Ala
 65                  70                  75                  80

Glu Glu Asn Leu Leu Val His Leu Lys Pro Val Glu Arg Cys Trp Gln
                 85                  90                  95

Pro Gln Asp Phe Leu Pro Asp Ser Ala Phe Glu Gly Phe His Glu Gln
                100                 105                 110

Val Arg Glu Leu Arg Glu Arg Ala Lys Glu Leu Pro Asp Glu Tyr Phe
            115                 120                 125

Val Val Leu Val Gly Asp Met Ile Thr Glu Glu Ala Leu Pro Thr Tyr
130                 135                 140

Gln Thr Met Leu Asn Thr Leu Asp Gly Val Arg Asp Glu Thr Gly Ala
145                 150                 155                 160

Ser Pro Thr Pro Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
                180                 185                 190

Val Asp Met Arg Gln Val Glu Lys Thr Ile Gln Tyr Leu Ile Gly Ser
            195                 200                 205

Gly Met Asp Pro Arg Thr Glu Asn Asn Pro Tyr Leu Gly Phe Ile Tyr
210                 215                 220

Thr Ser Phe Gln Glu Arg Ala Thr Phe Ile Ser His Gly Asn Thr Ala
225                 230                 235                 240

Arg Leu Ala Lys Glu His Gly Asp Ile Lys Leu Ala Gln Ile Cys Gly
                245                 250                 255

Thr Ile Thr Ala Asp Glu Lys Arg His Glu Thr Ala Tyr Thr Lys Ile
                260                 265                 270

Val Glu Lys Leu Phe Glu Ile Asp Pro Glu Gly Thr Val Ile Ala Phe
            275                 280                 285

Glu Glu Met Met Arg Lys Lys Val Ser Met Pro Ala His Leu Met Tyr
290                 295                 300

Asp Gly Arg Asp Asp Asn Leu Phe His His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Glu Ser Leu Thr Gly Leu Ser Gly Glu
                340                 345                 350

Gly Gln Lys Ala Gln Asp Tyr Val Cys Ala Leu Pro Ala Arg Ile Arg
            355                 360                 365

Lys Leu Glu Glu Arg Ala Gln Gly Arg Ala Lys Glu Gly Pro Thr Ile
370                 375                 380

Pro Phe Ser Trp Ile Phe Asp Arg Gln Val Lys Leu
385                 390                 395

<210> SEQ ID NO 19
<211> LENGTH: 374
<212> TYPE: PRT
<213> ORGANISM: Arabidopsis thaliana

<400> SEQUENCE: 19

Met Pro Ser Pro Ser Thr Phe Leu Ala Ser Arg Pro Arg Gly Pro Ala
 1               5                  10                  15

Lys Ile Ser Ala Val Ala Ala Pro Val Arg Pro Ala Leu Lys His Gln
             20                  25                  30
```

Asn Lys Ile His Thr Met Pro Pro Glu Lys Met Glu Ile Phe Lys Ser
            35                  40                  45

Leu Asp Gly Trp Ala Lys Asp Gln Ile Leu Pro Leu Leu Lys Pro Val
        50                  55                  60

Asp Gln Cys Trp Gln Pro Ala Ser Phe Leu Pro Asp Pro Ala Leu Pro
 65                  70                  75                  80

Phe Ser Glu Phe Thr Asp Gln Val Arg Glu Leu Arg Glu Arg Thr Ala
                85                  90                  95

Ser Leu Pro Asp Glu Tyr Phe Val Val Leu Val Gly Asp Met Ile Thr
            100                 105                 110

Glu Asp Ala Leu Pro Thr Tyr Gln Thr Met Ile Asn Thr Leu Asp Gly
        115                 120                 125

Val Arg Asp Glu Thr Gly Ala Ser Glu Ser Ala Trp Ala Ser Trp Thr
    130                 135                 140

Arg Ala Trp Thr Ala Glu Glu Asn Arg His Gly Asp Leu Leu Arg Thr
145                 150                 155                 160

Tyr Leu Tyr Leu Ser Gly Arg Val Asp Met Leu Met Val Glu Arg Thr
                165                 170                 175

Val Gln His Leu Ile Gly Ser Gly Met Asp Pro Gly Thr Glu Asn Asn
            180                 185                 190

Pro Tyr Leu Gly Phe Val Tyr Thr Ser Phe Gln Glu Arg Ala Thr Phe
        195                 200                 205

Val Ser His Gly Asn Thr Ala Arg Leu Ala Lys Ser Ala Gly Asp Pro
    210                 215                 220

Val Leu Ala Arg Ile Cys Gly Thr Ile Ala Ala Asp Glu Lys Arg His
225                 230                 235                 240

Glu Asn Ala Tyr Val Arg Ile Val Glu Lys Leu Leu Glu Ile Asp Pro
                245                 250                 255

Asn Gly Ala Val Ser Ala Val Ala Asp Met Met Arg Lys Lys Ile Thr
            260                 265                 270

Met Pro Ala His Leu Met Thr Asp Gly Arg Asp Pro Met Leu Phe Glu
        275                 280                 285

His Phe Ser Ala Val Ala Gln Arg Leu Glu Val Tyr Thr Ala Asp Asp
    290                 295                 300

Tyr Ala Asp Ile Leu Glu Phe Leu Val Gly Arg Trp Arg Leu Glu Lys
305                 310                 315                 320

Leu Glu Gly Leu Thr Gly Glu Gly Gln Arg Ala Gln Glu Phe Val Cys
                325                 330                 335

Gly Leu Ala Gln Arg Ile Arg Arg Leu Gln Glu Arg Ala Asp Glu Arg
            340                 345                 350

Ala Lys Lys Leu Lys Lys Thr His Glu Val Cys Phe Ser Trp Ile Phe
        355                 360                 365

Asp Lys Gln Ile Ser Val
    370

<210> SEQ ID NO 20
<211> LENGTH: 398
<212> TYPE: PRT
<213> ORGANISM: Simmondsia chinensis

<400> SEQUENCE: 20

Met Ala Leu Lys Leu His His Thr Ala Phe Asn Pro Ser Met Ala Val
 1               5                  10                  15

Thr Ser Ser Gly Leu Pro Arg Ser Tyr His Leu Arg Ser His Arg Val

-continued

```
                20                  25                  30
Phe Met Ala Ser Ser Thr Ile Gly Ile Thr Ser Lys Glu Ile Pro Asn
            35                  40                  45
Ala Lys Lys Pro His Met Pro Pro Arg Glu Ala His Val Gln Lys Thr
        50                  55                  60
His Ser Met Pro Pro Gln Lys Ile Glu Ile Phe Lys Ser Leu Glu Gly
65                  70                  75                  80
Trp Ala Glu Glu Asn Val Leu Val His Leu Lys Pro Val Glu Lys Cys
                85                  90                  95
Trp Gln Pro Gln Asp Phe Leu Pro Asp Pro Ala Ser Glu Gly Phe Met
            100                 105                 110
Asp Gln Val Lys Glu Leu Arg Glu Arg Thr Lys Glu Ile Pro Asp Glu
        115                 120                 125
Tyr Leu Val Leu Val Gly Asp Met Ile Thr Glu Glu Ala Leu Pro
    130                 135                 140
Thr Tyr Gln Thr Met Leu Asn Thr Leu Asp Gly Val Arg Asp Glu Thr
145                 150                 155                 160
Gly Ala Ser Leu Thr Ser Trp Ala Ile Trp Thr Arg Ala Trp Thr Ala
                165                 170                 175
Glu Glu Asn Arg His Gly Asp Leu Leu Asn Lys Tyr Leu Tyr Leu Thr
            180                 185                 190
Gly Arg Val Asp Met Lys Gln Ile Glu Lys Thr Ile Gln Tyr Leu Ile
        195                 200                 205
Gly Ser Gly Met Asp Pro Arg Ser Glu Asn Asn Pro Tyr Leu Gly Phe
    210                 215                 220
Ile Tyr Thr Ser Phe Gln Glu Arg Ala Thr Phe Ile Ser His Gly Asn
225                 230                 235                 240
Thr Ala Arg Leu Ala Lys Asp His Gly Asp Phe Gln Leu Ala Gln Val
                245                 250                 255
Cys Gly Ile Ile Ala Ala Asp Glu Lys Arg His Glu Thr Ala Tyr Thr
            260                 265                 270
Lys Ile Val Glu Lys Leu Phe Glu Ile Asp Pro Asp Gly Ala Val Leu
        275                 280                 285
Ala Leu Ala Asp Met Met Arg Lys Lys Val Ser Met Pro Ala His Leu
    290                 295                 300
Met Tyr Asp Gly Lys Asp Asn Leu Phe Glu Asn Tyr Ser Ala Val
305                 310                 315                 320
Ala Gln Gln Ile Gly Val Tyr Thr Ala Lys Asp Tyr Ala Asp Ile Leu
                325                 330                 335
Glu His Leu Val Asn Arg Trp Lys Val Glu Asn Leu Met Gly Leu Ser
            340                 345                 350
Gly Glu Gly His Lys Ala Gln Asp Phe Val Cys Gly Leu Ala Pro Arg
        355                 360                 365
Ile Arg Lys Leu Gly Glu Arg Ala Gln Ser Leu Ser Lys Pro Val Ser
    370                 375                 380
Leu Val Pro Phe Ser Trp Ile Phe Asn Lys Glu Leu Lys Val
385                 390                 395

<210> SEQ ID NO 21
<211> LENGTH: 411
<212> TYPE: PRT
<213> ORGANISM: Arabidopsis thaliana

<400> SEQUENCE: 21
```

```
Met Ala Leu Leu Leu Asn Ser Thr Ile Thr Val Ala Met Lys Gln Asn
  1               5                  10                  15

Pro Leu Val Ala Val Ser Phe Pro Arg Thr Thr Cys Leu Gly Ser Ser
             20                  25                  30

Phe Ser Pro Pro Arg Leu Leu Arg Val Ser Cys Val Ala Thr Asn Pro
         35                  40                  45

Ser Lys Thr Ser Glu Glu Thr Asp Lys Lys Phe Arg Pro Ile Lys
 50                  55                  60

Glu Val Pro Asn Gln Val Thr His Thr Ile Thr Gln Glu Lys Leu Glu
 65                  70                  75                  80

Ile Phe Lys Ser Met Glu Asn Trp Ala Gln Glu Asn Leu Leu Ser Tyr
                 85                  90                  95

Leu Lys Pro Val Glu Ala Ser Trp Gln Pro Gln Asp Phe Leu Pro Glu
            100                 105                 110

Thr Asn Asp Glu Asp Arg Phe Tyr Glu Gln Val Lys Glu Leu Arg Asp
        115                 120                 125

Arg Thr Lys Glu Ile Pro Asp Asp Tyr Phe Val Val Leu Val Gly Asp
        130                 135                 140

Met Ile Thr Glu Glu Ala Leu Pro Thr Tyr Gln Thr Thr Leu Asn Thr
145                 150                 155                 160

Leu Asp Gly Val Lys Asp Glu Thr Gly Gly Ser Leu Thr Pro Trp Ala
                165                 170                 175

Val Trp Val Arg Ala Trp Thr Ala Glu Glu Asn Arg His Gly Asp Leu
            180                 185                 190

Leu Asn Lys Tyr Leu Tyr Leu Ser Gly Arg Val Asp Met Arg His Val
        195                 200                 205

Glu Lys Thr Ile Gln Tyr Leu Ile Gly Ser Gly Met Asp Ser Lys Phe
210                 215                 220

Glu Asn Asn Pro Tyr Asn Gly Phe Ile Tyr Thr Ser Phe Gln Glu Arg
225                 230                 235                 240

Ala Thr Phe Ile Ser His Gly Asn Thr Ala Lys Leu Ala Thr Thr Tyr
                245                 250                 255

Gly Asp Thr Thr Leu Ala Lys Ile Cys Gly Thr Ile Ala Ala Asp Glu
            260                 265                 270

Lys Arg His Glu Thr Ala Tyr Thr Arg Ile Val Glu Lys Leu Phe Glu
        275                 280                 285

Ile Asp Pro Asp Gly Thr Val Gln Ala Leu Ala Ser Met Met Arg Lys
        290                 295                 300

Arg Ile Thr Met Pro Ala His Leu Met His Asp Gly Arg Asp Asp Asp
305                 310                 315                 320

Leu Phe Asp His Tyr Ala Ala Val Ala Gln Arg Ile Gly Val Tyr Thr
                325                 330                 335

Ala Thr Asp Tyr Ala Gly Ile Leu Glu Phe Leu Leu Arg Arg Trp Glu
            340                 345                 350

Val Glu Lys Leu Gly Met Gly Leu Ser Gly Glu Gly Arg Arg Ala Gln
        355                 360                 365

Asp Tyr Leu Cys Thr Leu Pro Gln Arg Ile Arg Arg Leu Glu Glu Arg
        370                 375                 380

Ala Asn Asp Arg Val Lys Leu Ala Ser Lys Ser Lys Pro Ser Val Ser
385                 390                 395                 400

Phe Ser Trp Ile Tyr Gly Arg Glu Val Glu Leu
                405                 410
```

-continued

<210> SEQ ID NO 22
<211> LENGTH: 396
<212> TYPE: PRT
<213> ORGANISM: Linum usitatissimum

<400> SEQUENCE: 22

```
Met Ala Leu Lys Leu Asn Pro Val Thr Thr Phe Pro Ser Thr Arg Ser
 1               5                  10                  15

Leu Asn Asn Phe Ser Ser Arg Ser Pro Arg Thr Phe Leu Met Ala Ala
             20                  25                  30

Ser Thr Phe Asn Ser Thr Ser Thr Lys Glu Ala Glu Lys Leu Lys Lys
         35                  40                  45

Ser His Gly Pro Pro Lys Glu Val His Met Gln Val Thr His Ser Met
     50                  55                  60

Pro Pro Gln Lys Leu Glu Ile Phe Lys Ser Leu Glu Gly Trp Ala Glu
 65                  70                  75                  80

Asp Val Leu Leu Pro His Leu Lys Pro Val Glu Lys Cys Trp Gln Pro
                 85                  90                  95

Gln Asp Phe Leu Pro Glu Pro Ser Asp Gly Phe Glu Glu Gln Val
            100                 105                 110

Lys Glu Leu Arg Ala Arg Ala Lys Glu Leu Pro Asp Asp Tyr Phe Val
            115                 120                 125

Val Leu Val Gly Asp Met Ile Thr Glu Ala Leu Pro Thr Tyr Gln
        130                 135                 140

Thr Met Leu Asn Thr Leu Asp Gly Val Arg Asp Glu Thr Gly Ala Ser
145                 150                 155                 160

Leu Thr Pro Trp Ala Ile Trp Thr Arg Ala Trp Thr Ala Glu Glu Asn
                165                 170                 175

Arg His Gly Asp Leu Leu Asn Lys Tyr Leu Tyr Leu Ser Gly Arg Val
            180                 185                 190

Asp Met Arg Gln Ile Glu Lys Thr Ile Gln Tyr Leu Ile Gly Ser Gly
        195                 200                 205

Met Asp Pro Lys Thr Glu Asn Asn Pro Tyr Leu Gly Phe Ile Tyr Thr
    210                 215                 220

Ser Phe Gln Glu Arg Ala Thr Phe Ile Ser His Gly Asn Thr Ala Arg
225                 230                 235                 240

Leu Ala Lys Asp His Gly Asp Met Lys Leu Ala Gln Ile Cys Gly Ile
                245                 250                 255

Ile Ala Ala Asp Glu Lys Arg His Glu Thr Ala Tyr Thr Lys Ile Val
            260                 265                 270

Glu Lys Leu Phe Glu Ile Asp Pro Asp Gly Thr Val Leu Ala Leu Ala
        275                 280                 285

Asp Met Met Arg Lys Lys Ile Ser Met Pro Ala His Leu Met Tyr Asp
    290                 295                 300

Gly Glu Asp Asp Asn Leu Phe Asp Asn Tyr Ser Ser Val Ala Gln Arg
305                 310                 315                 320

Ile Gly Val Tyr Thr Ala Lys Asp Tyr Ala Asp Ile Leu Glu Phe Leu
                325                 330                 335

Val Gly Arg Trp Lys Val Asp Ala Phe Thr Gly Leu Ser Gly Glu Gly
            340                 345                 350

Asn Lys Ala Gln Asp Phe Val Cys Gly Leu Pro Ala Arg Ile Arg Lys
        355                 360                 365

Leu Glu Glu Arg Ala Ala Gly Arg Ala Lys Gln Thr Ser Lys Ser Val
    370                 375                 380
```

Pro Phe Ser Trp Ile Phe Ser Arg Glu Leu Val Leu
385                 390                 395

<210> SEQ ID NO 23
<211> LENGTH: 391
<212> TYPE: PRT
<213> ORGANISM: Glycine max

<400> SEQUENCE: 23

Met ala Leu Arg Leu Asn Pro Ile Pro Thr Gln Thr Phe Ser Leu Pro
1               5                   10                  15

Gln Met Pro Ser Leu Arg Ser Pro Arg Phe Arg Met ala Ser Thr Leu
            20                  25                  30

Arg Ser Gly Ser Lys Glu Val Glu Asn Ile Lys Lys Pro Phe Thr Pro
        35                  40                  45

Pro Arg Glu Val His Val Gln Val Thr His Ser Met Pro Pro Gln Lys
    50                  55                  60

Ile Glu Ile Phe Lys Ser Leu Glu Asp Trp Ala Asp Gln Asn Ile Leu
65                  70                  75                  80

Thr His Leu Lys Pro Val Glu Lys Cys Trp Gln Pro Gln Asp Phe Leu
                85                  90                  95

Pro Asp Pro Ser Ser Asp Gly Phe Glu Glu Gln Val Lys Glu Leu Arg
            100                 105                 110

Glu Arg Ala Lys Glu Ile Pro Asp Asp Tyr Phe Val Leu Val Gly
        115                 120                 125

Asp Met Ile Thr Glu Glu Ala Leu Pro Thr Tyr Gln Thr Met Leu Asn
130                 135                 140

Thr Leu Asp Gly Val Arg Asp Glu Thr Gly Ala Ser Leu Thr Ser Trp
145                 150                 155                 160

Ala Ile Trp Thr Arg Ala Trp Thr Ala Glu Glu Asn Arg His Gly Asp
                165                 170                 175

Leu Leu Asn Lys Tyr Leu Tyr Leu Ser Gly Arg Val Asp Met Lys Gln
            180                 185                 190

Ile Glu Lys Thr Ile Gln Tyr Leu Ile Gly Ser Gly Met Asp Pro Arg
        195                 200                 205

Thr Glu Asn Ser Pro Tyr Leu Gly Phe Ile Tyr Thr Ser Phe Gln Glu
210                 215                 220

Arg Ala Thr Phe Ile Ser His Gly Asn Thr Ala Arg Leu Ala Lys Glu
225                 230                 235                 240

His Gly Asp Ile Lys Leu Ala Gln Ile Cys Gly Met Ile Ala Ser Asp
                245                 250                 255

Glu Lys Arg His Glu Thr Ala Tyr Thr Lys Ile Val Glu Lys Leu Phe
            260                 265                 270

Glu Val Asp Pro Asp Gly Thr Val Met ala Phe Ala Asp Met Met Arg
        275                 280                 285

Lys Lys Ile Ala Met Pro Ala His Leu Met Tyr Asp Gly Arg Asp Asp
290                 295                 300

Asn Leu Phe Asp Asn Tyr Ser Ala Val Ala Gln Arg Ile Gly Val Tyr
305                 310                 315                 320

Thr Ala Lys Asp Tyr Ala Asp Ile Leu Glu Phe Leu Val Gly Arg Trp
                325                 330                 335

Lys Val Glu Gln Leu Thr Gly Leu Ser Gly Glu Gly Arg Lys Ala Gln
            340                 345                 350

Glu Tyr Val Cys Gly Leu Pro Pro Arg Ile Arg Arg Leu Glu Glu Arg
        355                 360                 365

```
Ala Gln Ala Arg Gly Lys Glu Ser Ser Thr Leu Lys Phe Ser Trp Ile
    370                 375                 380

His Asp Arg Glu Val Leu Leu
385                 390

<210> SEQ ID NO 24
<211> LENGTH: 80
<212> TYPE: DNA
<213> ORGANISM: Artificial Sequence
<220> FEATURE:
<223> OTHER INFORMATION: Description of Artificial Sequence:
      ELVISLIVES complementary region of pKS106 and pKS124

<400> SEQUENCE: 24
cggccggagc tggtcatctc gctcatcgtc gagtcggcgg ccgccgactc gacgatgagc       60
gagatgacca gctccggccg                                                  80

<210> SEQ ID NO 25
<211> LENGTH: 154
<212> TYPE: DNA
<213> ORGANISM: Artificial Sequence
<220> FEATURE:
<223> OTHER INFORMATION: Description of Artificial Sequence:
      ELVISLIVES complementary region of pKS133

<400> SEQUENCE: 25
cggccggagc tggtcatctc gctcatcgtc gagtcggcgg ccggagctgg tcatctcgct       60
catcgtcgag tcggcggccg ccgactcgac gatgagcgag atgaccagct ccggccgccg      120
actcgacgat gagcgagatg accagctccg gccg                                  154

<210> SEQ ID NO 26
<211> LENGTH: 6611
<212> TYPE: DNA
<213> ORGANISM: Plasmid pBS68
<220> FEATURE:
<221> NAME/KEY: Unsure
<222> LOCATION: (4436)..(4436)
<223> OTHER INFORMATION: n = A, C, G, or T

<400> SEQUENCE: 26
cgcgcctatg cgggaccatc gcagcggacg agaagcggca cgagaacgcg tactcaagaa       60
tcgtggagaa gcttctggaa gtggaccccca ccggggcaat ggtggccata gggaacatga     120
tggagaagaa gatcacgatg ccggcgcacc ttatgtacga tggggatgac cccaggctat     180
tcgagcacta ctccgctgtg gcgcagcgca taggcgtgta caccgccaac gactacgcag     240
acatcttgga tttctcgttg acggtgaaga ttggagaagc ttgaaggatt gatgcctgag     300
gggaagcggg ccccaggatt tccgtgtgtg ggttgccccc gaggattagg aggttccaag     360
aacgcgctga tgagcgagcg cgtaagatga agaagcatca tgccgttaag ttcagttgga     420
ttttcaataa agaattgctt ttgtgagcgg ccgccgactc gacgatgagc gagatgacca     480
gctccggccg ccgactcgac gatgagcgag atgaccagct ccggccgcga cacaagtgtg     540
agagtactaa ataaatgctt tggttgtacg aaatcattac actaaataaa ataatcaaag     600
cttatatatg ccttccgcta aggccgaatc caaagaaatt ggttctttct cgttatcttt     660
tgccactttt actagtacgt attaattact acttaatcat ctttgtttac ggctcattat     720
atccgtcgac ggcgcgcccg atcatccgga tatagttcct cctttcagca aaaaaccect     780 caagacccgt ttagaggccc caaggggtta tgctagttat tgctcagcgg tggcagcagc     840
```

```
caactcagct tcctttcggg ctttgttagc agccggatcg atccaagctg tacctcacta    900
ttcctttgcc ctcggacgag tgctggggcg tcggtttcca ctatcggcga gtacttctac    960
acagccatcg gtccagacgg ccgcgcttct gcgggcgatt tgtgtacgcc cgacagtccc   1020
ggctccggat cggacgattg cgtcgcatcg accctgcgcc aagctgcat catcgaaatt    1080
gccgtcaacc aagctctgat agagttggtc aagaccaatg cggagcatat acgcccggag   1140
ccgcggcgat cctgcaagct ccggatgcct ccgctcgaag tagcgcgtct gctgctccat   1200
acaagccaac cacggcctcc agaagaagat gttggcgacc tcgtattggg aatccccgaa   1260
catcgcctcg ctccagtcaa tgaccgctgt tatgcggcca ttgtccgtca ggacattgtt   1320
ggagccgaaa tccgcgtgca cgaggtgccg gacttcgggg cagtcctcgg cccaaagcat   1380
cagctcatcg agagcctgcg cgacggacgc actgacggtg tcgtccatca cagtttgcca   1440
gtgatacaca tggggatcag caatcgcgca tatgaaatca cgccatgtag tgtattgacc   1500
gattccttgc ggtccgaatg ggccgaaccc gctcgtctgg ctaagatcgg ccgcagcgat   1560
cgcatccata gcctccgcga ccggctgcag aacagcgggc agttcggttt caggcaggtc   1620
ttgcaacgtg acccctgtg cacggcggga gatgcaatag gtcaggctct cgctgaattc    1680
cccaatgtca agcacttccg gaatcgggag cgcggccgat gcaaagtgcc gataaacata   1740
acgatctttg tagaaaccat cggcgcagct atttacccgc aggacatatc cacgccctcc   1800
tacatcgaag ctgaaagcac gagattcttc gccctccgag agctgcatca ggtcggagac   1860
gctgtcgaac ttttcgatca gaaacttctc gacagacgtc gcggtgagtt caggcttttc   1920
catgggtata tctccttctt aaagttaaac aaaattattt ctagagggaa accgttgtgg   1980
tctccctata gtgagtcgta ttaatttcgc gggatcgaga tctgatcaac ctgcattaat   2040
gaatcggcca acgcgcgggg agaggcggtt tgcgtattgg gcgctcttcc gcttcctcgc   2100
tcactgactc gctgcgctcg gtcgttcggc tgcggcgagc ggtatcagct cactcaaagg   2160
cggtaatacg gttatccaca gaatcagggg ataacgcagg aaagaacatg tgagcaaaag   2220
gccagcaaaa ggccaggaac cgtaaaaagg ccgcgttgct ggcgtttttc cataggctcc   2280
gcccccctga cgagcatcac aaaaatcgac gctcaagtca gaggtggcga acccgacag    2340
gactataaag ataccaggcg tttccccctg gaagctccct cgtgcgctct cctgttccga   2400
ccctgccgct taccggatac ctgtccgcct ttctcccttc gggaagcgtg gcgctttctc   2460
aatgctcacg ctgtaggtat ctcagttcgg tgtaggtcgt tcgctccaag ctgggctgtg   2520
tgcacgaacc ccccgttcag cccgaccgct gcgccttatc cggtaactat cgtcttgagt   2580
ccaacccggt aagacacgac ttatcgccac tggcagcagc cactggtaac aggattagca   2640
gagcgaggta tgtaggcggt gctacagagt tcttgaagtg gtggcctaac tacggctaca   2700
ctagaaggac agtatttggt atctgcgctc tgctgaagcc agttaccttc ggaaaaagag   2760
ttggtagctc ttgatccggc aaacaaacca ccgctggtag cggtggtttt tttgtttgca   2820
agcagcagat tacgcgcaga aaaaaggat ctcaagaaga tcctttgatc ttttctacgg    2880
ggtctgacgc tcagtggaac gaaaactcac gttaagggat tttggtcatg acattaacct   2940
ataaaaatag gcgtatcacg aggccctttc gtctcgcgcg tttcggtgat gacggtgaaa   3000
acctctgaca catgcagctc ccggagacgt cacagcttg tctgtaagcg gatgccggga    3060
gcagacaagc ccgtcagggc gcgtcagcgg gtgttggcgg gtgtcggggc tggcttaact   3120
atgcggcatc agagcagatt gtactgagag tgcaccatat ggacatattg tcgttagaac   3180
gcggctacaa ttaatacata accttatgta tcatacacat acgatttagg tgacactata   3240
```

```
gaacggcgcg ccaagcttgg atcctcgaag agaagggtta ataacacatt ttttaacatt    3300
tttaacacaa attttagtta tttaaaaatt tattaaaaaa tttaaaataa gaagaggaac    3360
tctttaaata aatctaactt acaaaattta tgattttaa taagttttca ccaataaaaa     3420
atgtcataaa aatatgttaa aaagtatatt atcaatattc tctttatgat aaataaaaag    3480
aaaaaaaaaa taaagttaa gtgaaaatga gattgaagtg actttaggtg tgtataaata    3540
tatcaacccc gccaacaatt tatttaatcc aaatatattg aagtatatta ttccatagcc    3600
tttatttatt tatatattta ttatataaaa gctttatttg ttctaggttg ttcatgaaat    3660 attttttgg ttttatctcc gttgtaagaa aatcatgtgc tttgtgtcgc cactcactat     3720
tgcagctttt tcatgcattg gtcagattga cggttgattg tattttgtt ttttatggtt     3780 ttgtgttatg acttaagtct tcatctcttt atctcttcat caggtttgat ggttacctaa    3840
tatggtccat gggtacatgc atggttaaat taggtggcca actttgttgt gaacgataga    3900 attttttta tattaagtaa actattttta tattatgaaa taataataaa aaaaatattt    3960
tatcattatt aacaaaatca tattagttaa tttgttaact ctataataaa agaaatactg    4020
taacattcac attacatggt aacatctttc caccctttca tttgttttt gtttgatgac    4080 ttttttctt gtttaaattt atttcccttc ttttaaattt ggaatacatt atcatcatat     4140
ataaactaaa atactaaaaa caggattaca caaatgataa ataataacac aaatatttat    4200
aaatctagct gcaatatatt taaactagct atatcgatat tgtaaaataa aactagctgc    4260
attgatactg ataaaaaaat atcatgtgct ttctggactg atgatgcagt atacttttga    4320
cattgccttt atttttttt tcagaaaagc tttcttagtt ctgggttctt cattatttgt      4380
ttcccatctc cattgtgaat tgaatcattt gcttcgtgtc acaaatacaa tttagntagg    4440
tacatgcatt ggtcagattc acggtttatt atgtcatgac ttaagttcat ggtagtacat    4500
tacctgccac gcatgcatta tattggttag atttgatagg caaatttggt tgtcaacaat    4560 ataatataa ataatgtttt tatattacga aataacagtg atcaaaacaa acagttttat    4620
ctttattaac aagattttgt ttttgtttga tgacgttttt taatgtttac gctttccccc    4680
ttcttttgaa tttagaacac tttatcatca taaaatcaaa tactaaaaaa attacatatt    4740
tcataaataa taacacaaat atttttaaaa aatctgaaat aataatgaac aatattacat    4800
attatcacga aaattcatta ataaaaatat tatataaata aaatgtaata gtagttatat    4860
gtaggaaaaa agtactgcac gcataatata tacaaaaaga ttaaaatgaa ctattataaa    4920
taataacact aaattaatgg tgaatcatat caaaataatg aaaaagtaaa taaaatttgt    4980
aattaacttc tatatgtatt acacacacaa ataataaata atagtaaaaa aaattatgat    5040
aaatatttac catctcataa gatatttaaa ataatgataa aaatatagat tatttttat     5100 gcaactagct agccaaaaag agaacacggg tatatataaa aagagtacct ttaaattcta    5160
ctgtacttcc tttattcctg acgttttat atcaagtgga catacgtgaa gatttaatt      5220 atcagtctaa atatttcatt agcacttaat acttttctgt tttattccta tcctataagt    5280
agtcccgatt ctcccaacat tgcttattca cacaactaac taagaaagtc ttccatagcc    5340
ccccaagcgg ccggagctgg tcatctcgct catcgtcgag tcggcggccg gagctggtca    5400
tctcgctcat cgtcgagtcg gcggccgctg agtgattgct cacgagtgtg gtcaccatgc    5460
cttcagcaag taccaatggg ttgatgatgt tgtgggtttg acccttcact caacactttt    5520
agtcccttat ttctcatgga aaataagcca tcgccgccac cactccaaca caggttccct    5580
```

```
                                                                 -continued
tgaccgtgat gaagtgtttg tcccaaaacc aaaatccaaa gttgcatggt tttccaagta    5640
cttaaacaac cctctaggaa gggctgtttc tcttctcgtc acactcacaa tagggtggcc    5700
tatgtattta gccttcaatg tctctggtag accctatgat agttttgcaa gccactacca    5760
cccttatgct cccatatatt ctaaccgtga gaggcttctg atctatgtct ctgatgttgc    5820
tttgttttct gtgacttact ctctctaccg tgttgcaacc ctgaaagggt tggtttggct    5880
gctatgtgtt tatggggtgc ctttgctcat tgtgaacggt tttcttgtga ctatcacata    5940
tttgcagcac acacactttg ccttgcctca ttacgattca tcagaatggg actggctgaa    6000
gggagctttg gcaactatgg acagagatta agcggccgca tgcctccaga aaagaaagaa    6060
attttcaagt ccttggaggg atgggcctcg gagtgggtcc taccgctgct gaagcccgtg    6120
gagcaatgct ggcagccaca aaacttcctc cctgacccct cccttccgca tgaagagttc    6180
agccatcagg tgaaggagct tcgcgaacgc actaaagagt tacctgatga gtactttgtg    6240
gtgctggtgg gtgatatggt caccgaggac gcgcttccca cttaccagac catgatcaac    6300
aaccttgatg gagtgaaaga tgacagcggc acgagcccga gcccgtgggc cgtgtggacc    6360
cgggcctgga ccgccgagga aaacagacac ggggatctgc tcagaactta tttgtatctc    6420
tctgggaggg ttgacatggc taaggtcgaa aagaccgtac attacctcat ttcagctggc    6480
atggaccctg ggacagacaa caacccatat ttggggtttg tgtacacgtc attccaagag    6540
cgagcaacat ttgtggcgca cgggaacacg gctcggctcg cgaaggaggg cggggatcca    6600
gtgctggcgc g                                                         6611
```